(12) United States Patent
Edwards et al.

(10) Patent No.: US 12,327,639 B2
(45) Date of Patent: Jun. 10, 2025

(54) METHODS AND APPARATUS FOR INSULIN DOSING GUIDANCE AND DECISION SUPPORT FOR DIABETIC PATIENT EXERCISE

(71) Applicant: Eli Lilly and Company, Indianapolis, IN (US)

(72) Inventors: Stephanie Smith Edwards, Milton, MA (US); Michelle Lynne Katz, Newton, MA (US); Michael Charles Riddell, Toronto (CA); Howard Allan Wolpert, Brookline, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 194 days.

(21) Appl. No.: 17/598,539

(22) PCT Filed: Mar. 26, 2020

(86) PCT No.: PCT/US2020/024835
§ 371 (c)(1),
(2) Date: Sep. 27, 2021

(87) PCT Pub. No.: WO2020/205393
PCT Pub. Date: Oct. 8, 2020

(65) Prior Publication Data
US 2022/0172842 A1    Jun. 2, 2022

Related U.S. Application Data

(60) Provisional application No. 62/827,350, filed on Apr. 1, 2019.

(51) Int. Cl.
*G16H 50/20*    (2018.01)
*A61B 5/00*    (2006.01)
(Continued)

(52) U.S. Cl.
CPC ............ *G16H 50/20* (2018.01); *A61B 5/1118* (2013.01); *A61B 5/14532* (2013.01);
(Continued)

(58) Field of Classification Search
CPC ........ G16H 50/20; G16H 50/30; G16H 20/30; A61B 5/1118; A61B 5/14532; A61B 5/6898; A61B 5/742
See application file for complete search history.

(56) References Cited

U.S. PATENT DOCUMENTS 9,199,031 B2    12/2015    Yodfat et al.
10,105,093 B2    10/2018    Schabbach et al.
(Continued)

FOREIGN PATENT DOCUMENTS

IN        282517 B        9/2009
WO        2007138154        12/2007
(Continued)

OTHER PUBLICATIONS

Goode, A., et al., "A Practical Cyber-Physical System for the Self-Capture of the Effect of Exercise on Blood Glucose Levels," 2017 IEEE 15$^{th}$ Int'l Conf on Dependable, Autonomic and Secure Computing, 15$^{th}$ Int'l Conf on Pervasive Intelligence and Computing, 3rd Int'l Conf on Big Data Intelligence and Computing and Cyber Science and Technology Congress, DASC/PICOM/DATACOM/CYBERSCI, Nov. 6, 2017, pp. 245-250.
(Continued)

*Primary Examiner* — Matthew Kremer
*Assistant Examiner* — Evelyn Grace Park
(74) *Attorney, Agent, or Firm* — Arthur Shum

(57) ABSTRACT

The techniques described herein relate to computerized methods and apparatus for insulin dosing guidance and decision support for diabetic patients. The techniques can recommend one or more exercises to a diabetic patient. The
(Continued)

techniques can recommend adjustments to a diabetes treatment plan based on a diabetic patients planned exercise. The techniques can provide recommendations to a diabetic patient while exercising. The techniques can customize a computerized exercise planning tool that is used to develop an exercise plan for a diabetic patient based on user preference data of the diabetic patient, data indicative of a treatment aspect of the diabetic patient, data indicative of a physiological aspect of the patient, or some combination thereof.

21 Claims, 46 Drawing Sheets

(51) Int. Cl.
  *A61B 5/11* (2006.01)
  *A61B 5/145* (2006.01)
  *G16H 50/30* (2018.01)
(52) U.S. Cl.
  CPC ............ *A61B 5/6898* (2013.01); *A61B 5/742* (2013.01); *G16H 50/30* (2018.01)

(56) References Cited

U.S. PATENT DOCUMENTS

| | | | |
|---|---|---|---|
| 2016/0106363 A1* | 4/2016 | O'Connell | ............ G16H 40/63 600/301 |
| 2016/0263439 A1 | 9/2016 | Ackland | |
| 2017/0100635 A1 | 4/2017 | Takeuchi et al. | |
| 2017/0372017 A1 | 12/2017 | Steffen | |
| 2018/0099092 A1* | 4/2018 | Roy | .................... A61M 5/1723 |
| 2018/0226140 A1 | 8/2018 | Booth et al. | |
| 2019/0252079 A1* | 8/2019 | Constantin | ......... A61B 5/14532 |

FOREIGN PATENT DOCUMENTS

| | | |
|---|---|---|
| WO | 2016061550 | 4/2016 |
| WO | 2018071579 | 4/2018 |
| WO | 2019157102 | 8/2019 |

OTHER PUBLICATIONS

Lloyd, et al., "iDecide: A Mobile Application for Insulin Dosing Using an Evidence Based Equation to Account for Patient Preferences," Studies in Health Technology and Informatics, vol. 216 (2015); 93-7.

Riddell, M., et al., "Exercise Management in Type 1 Diabetes: A Consensus Statement," Lancet Diabetes Endocrinol., May 2017; vol. 5, pp. 377-390.

Patent Cooperation Treaty International Search Report pertaining to International Application No. PCT/US2020/024835, International Filing Date: Mar. 26, 2020, Date of Mailing: Sep. 8, 2020.

Patent Cooperation Treaty Written Opinion of the International Searching Authority pertaining to International Application No. PCT/US2020/024835, International Filing Date: Mar. 26, 2020, Date of Mailing: Sep. 8, 2020.

* cited by examiner

540

| BASAL ADJUSTMENT (A) | |
|---|---|
| GLUCOSE READING (542) | RECOMMENDATION (544) |
| ≤ 90 mg/dL | 16g Glucose Tabs & Reduce Basal by 80% starting now through exercise duration. |
| 91-150 mg/dL | Reduce Basal by 80% starting now through exercise duration. |
| 151-250 mg/dL | Reduce Basal by 80% starting now through exercise duration. |
| ≥ 250 mg/dL | No Basal Rate Reduction If ketones are present, reschedule activity. If ketones are low or not present, mild exercise can begin. |

FIG. 5C

| BOLUS ADJUSTMENT | | |
|---|---|---|
| EXERCISE INTENSITY | 30 - 60 MINS | > 60 MINS |
| Mild | Reduce bolus by 25% | Reduce bolus by 50% |
| Moderate | Reduce bolus by 50% | Reduce bolus by 75% |
| Vigorous | Reduce bolus by 75% | |
| If glucose is ≥ 250 mg/dL | No Bolus Reduction. | |

FIG. 5E

| 1HR PRE-ACTIVITY | | |
|---|---|---|
| GLUCOSE READING | PUMP | NO PUMP |
| ≤ 90 mg/dL | 16g Glucose Tabs | |
| 91-150 mg/dL | No Recommendation | |
| 151-250 mg/dL | Temporarily increase Basal Rate by 20% until glucose is 120 - 150 mg/dL | No Recommendation |
| ≥ 250 mg/dL | If ketones are present, perform corrective action(bolus) and reschedule activity. If ketones are low or not present, mild exercise can begin (anaerobic discouraged). | |

| BASAL ADJUSTMENT (A) | |
|---|---|
| GLUCOSE READING (742) | RECOMMENDATION (744) |
| ≤ 90 mg/dL | 16g Glucose Tabs & Reduce Basal by 50% starting now through exercise duration. Consider stating with anaerobic. |
| 91-150 mg/dL | Reduce Basal by 50% starting now through exercise duration. Consider starting with anaerobic. |
| 151-250 mg/dL | Reduce Basal by 50% starting now through exercise duration. Start aerobic first. |
| ≥ 250 mg/dL | No Basal Rate Reduction If ketones are present, reschedule activity. If ketones are low or not present, mild exercise can begin. |

FIG. 7C

| BASAL ADJUSTMENT (B) | |
|---|---|
| GLUCOSE READING | RECOMMENDATION |
| ≤ 90 mg/dL | 16g Glucose Tabs & Reduce Basal by 40% starting now through exercise duration. Consider stating with anaerobic. |
| 91-150 mg/dL | Reduce Basal by 40% starting now through exercise duration. Consider starting with anaerobic. |
| 151-250 mg/dL | No Basal Reduction. Consider aerobic first. |
| ≥ 250 mg/dL | If ketones are present, reschedule activity. If ketones are low or not present, mild exercise can begin. |

FIG. 7D

760 — BASAL ADJUSTMENT (C)

RECOMMENDATION

Reduce Basal rate by 50% starting 90 minutes before exercise start time through exercise duration. Do not reduce if glucose is ≥ 250 mg/dL at time of reduction.

770 — BASAL ADJUSTMENT (D)

RECOMMENDATION

Reduce Basal rate by 40% starting 90 minutes before exercise start time through exercise duration. Do not reduce if glucose is ≥ 150 mg/dL at time of reduction.

FIG. 7E

| BOLUS ADJUSTMENT | | |
|---|---|---|
| EXERCISE INTENSITY | 30 - 60 MINS | > 60 MINS |
| Mild | N/A | N/A |
| Moderate | Reduce bolus by 20% | Reduce bolus by 40% |
| Vigorous | | |
| If glucose is ≥ 250 mg/dL | No Bolus Reduction | |

| 1HR CARB INTAKE | |
|---|---|
| GLUCOSE READING (802) | RECOMMENDATION (804) |
| ≤ 90 mg/dL | 16g Now |
| 91-150 mg/dL | No recommendation |
| 151-250 mg/dL | No recommendation |
| ≥ 250 mg/dL | If ketones are present, reschedule activity. If ketones are low or not present, mild exercise can begin. |

FIG. 8A

| 1HR PRE-ACTIVITY | | |
|---|---|---|
| GLUCOSE READING | PUMP | NO PUMP |
| ≤ 90 mg/dL | 16g Glucose Tabs ||
| 91-150 mg/dL | No recommendation ||
| 151-250 mg/dL | Temporarily increase Basal Rate by 20% until glucose is 120 - 150 mg/dL | No recommendation |
| ≥ 250 mg/dL | If ketones are present, perform corrective action (bolus) and reschedule activity. If ketones are low or not present, mild exercise can begin (anaerobic discouraged). ||

1HR CARB INTAKE

| GLUCOSE READING | RECOMMENDATION |
|---|---|
| ≤ 90 mg/dL | 16g Now |
| 91-150 mg/dL | No recommendation |
| 151-250 mg/dL | No recommendation |
| ≥ 250 mg/dL | If ketones are present, reschedule activity. If ketones are low or not present, mild exercise can begin. |

822 — GLUCOSE READING column; 824 — RECOMMENDATION column

FIG. 8C

| 15M CARB INTAKE (B) | | | |
|---|---|---|---|
| GLUCOSE READING | MILD | MODERATE | VIGOROUS |
| ≤ 90 mg/dL | 16g now + 0.0016g/kg/min during exercise | 16g now + 0.003g/kg/min during exercise | 16g now + 0.005g/kg/min during exercise |
| 91-150 mg/dL | 0.0016g/kg/min during exercise | 0.003g/kg/min during exercise | 0.005g/kg/min during exercise |
| 151-250 mg/dL | Delay carb feeding until glucose is under 150. | | |
| ≥ 250 mg/dL | If ketones are present, reschedule activity. If ketones are low or not present, mild to moderate aerobic exercise can begin. Delay carb feeding until glucose is under 150. | | |

FIG. 9B

| 15M CARB INTAKE (C) ||
|---|---|
| GLUCOSE READING | RECOMMENDATION |
| ≤ 90 mg/dL | 16g Now |
| 91-150 mg/dL | No recommendation. |
| 151-250 mg/dL | Consider mild/moderate aerobic exercise. |
| ≥ 250 mg/dL | If ketones are present, reschedule activity. If ketones are low or not present, mild exercise can begin. |

FIG. 9C

| 15M CARB INTAKE (D) | MILD | MODERATE | VIGOROUS |
|---|---|---|---|
| GLUCOSE READING | | | |
| ≤ 90 mg/dL | 16g now + 0.0041g/kg/min during exercise | 16g now + 0.0083g/kg/min during exercise | 16g now + 0.0125g/kg/min during exercise |
| 91-150 mg/dL | 0.0041g/kg/min during exercise | 0.0083g/kg/min during exercise | 0.0125g/kg/min during exercise |
| 151-250 mg/dL | Delay carb feeding until glucose is under 150. | | |
| ≥ 250 mg/dL | If ketones are present, reschedule activity. If ketones are low or not present, mild to moderate aerobic exercise can begin. Delay carb feeding until glucose is under 150. | | |

FIG. 9D

| 15M PRE-ACTIVITY | | |
|---|---|---|
| GLUCOSE READING | PUMP | NO PUMP |
| ≤ 90 mg/dL | 16g Glucose Tabs | |
| 91-150 mg/dL | No Recommendation | |
| 151-250 mg/dL | Consider aerobic warmup | |
| ≥ 250 mg/dL | If ketones are present, perform corrective action(bolus) and reschedule activity. If ketones are low or not present, mild exercise can begin (anaerobic discouraged). | |

FIG. 10

15M CARB INTAKE (A)

| GLUCOSE READING | RECOMMENDATION |
|---|---|
| ≤ 90 mg/dL | 16g Glucose Tabs + 0.004g/kg/min<br>Consider resistance first. |
| 91-150 mg/dL | 0.004g/kg/min<br>Consider resistance first. |
| 151-250 mg/dL | Consider aerobic first.<br>Delay carb feeding until on target. |
| ≥ 250 mg/dL | If ketones are present, reschedule activity (usual care, correction dose). If ketones are low or not present, consider aerobic first. |

| GLUCOSE READING | RECOMMENDATION |
|---|---|
| 15M CARB INTAKE (B) | |
| ≤ 90 mg/dL | 16g Glucose Tabs + 0.00584g/kg/min<br>Consider resistance first. |
| 91-150 mg/dL | 0.00584g/kg/min<br>Consider resistance first. |
| 151-250 mg/dL | Consider aerobic first.<br>Delay carb feeding until on target. |
| ≥ 250 mg/dL | If ketones are present, reschedule activity (usual care, correction dose). If ketones are low or not present, consider aerobic first. |

1102 — GLUCOSE READING; 1104 — RECOMMENDATION

| 15M CARB INTAKE (C) | |
|---|---|
| GLUCOSE READING (1122) | RECOMMENDATION (1124) |
| ≤ 90 mg/dL | 16g Glucose Tabs |
| 91-150 mg/dL | Consider anaerobic/resistance first. |
| 151-250 mg/dL | Consider aerobic first. |
| ≥ 250 mg/dL | If ketones are present, reschedule activity (usual care, correction dose). If ketones are low or not present, consider aerobic first. |

| 15M POST ACTIVITY | |
|---|---|
| GLUCOSE READING | RECOMMENDATION |
| ≤ 90 mg/dL | 16g Glucose Tabs<br>Resume usual Basal & Bolus patterns |
| 91-150 mg/dL | Resume usual Basal & Bolus patterns |
| 151-250 mg/dL | Consider aerobic cooldown or a<br>50% insulin bolus correction |
| ≥ 250 mg/dL | If ketones are present, perform sick days rules. If ketones are absent, perform 50% insulin bolus correction |

| 15M POST ACTIVITY | |
|---|---|
| GLUCOSE READING | RECOMMENDATION |
| ≤ 90 mg/dL | 16g Glucose Tabs<br>Resume usual Basal & Bolus patterns |
| 91-150 mg/dL | Resume usual Basal & Bolus patterns |
| 151-250 mg/dL | Consider aerobic cooldown or a<br>50% insulin bolus correction |
| ≥ 250 mg/dL | If ketones are present, perform sick days<br>rules. If ketones are absent, perform 50%<br>insulin bolus correction |

FIG. 12C

METHODS AND APPARATUS FOR INSULIN DOSING GUIDANCE AND DECISION SUPPORT FOR DIABETIC PATIENT EXERCISE

BACKGROUND

The pancreas regulates a person's glucose levels, but people with diabetes typically have a diminished ability to regulate their own glucose levels. If glucose levels drop too low, patients can enter a dangerous condition called hypoglycemia. If their glucose levels go too high, patients can enter another dangerous condition called hyperglycemia. Therefore, people with diabetes need to keep their glucose levels within a target ideal range by dosing themselves with insulin (which lowers glucose levels) or by ingesting carbohydrates and/or dosing themselves with glucagon (which raises glucose levels). Insulin can be administered in various forms, including through injections and/or using a pump. For example, insulin can be administered as a discrete dose that is injected all at once (e.g., a long-acting basal dose, or a bolus dose), or through a steady trickle that is infused using a pump over a period of multiple minutes or hours. Too much insulin can decrease glucose levels too much, sending patients into hypoglycemia. Too little insulin can leave glucose levels too high, sending patients into hyperglycemia. Therefore, diabetic patients have to dose themselves with the right amount of insulin, and at the right time.

Exercise is important for diabetic patients, but can affect a diabetic patient's glucose levels in complicated ways. For instance, aerobic exercise (e.g., light jogging) can decrease a patient's glucose levels. Exactly how much of a decrease, and when this decrease is expected to occur, can depend on various factors, such as the intensity and type of exercise. Conversely, anaerobic exercise (e.g., weight-lifting, sprinting) can increase a patient's glucose levels in the short term. Exactly how much of an increase can also depend on various factors, such as the intensity and type of exercise. The effects of exercise on a patient's glucose levels can occur both during and after the exercise has ended, sometimes many hours afterward. Therefore, for patients with diabetes, exercising can involve complicated decisions such as decisions around when and how to adjust their insulin doses, whether and when to ingest additional carbohydrates to offset decreases in glucose levels, and/or when to check their glucose levels.

SUMMARY

The present disclosure relates to techniques for planning for and performing exercises for users with diabetes (e.g., referred to as "users" and/or "patients" interchangeably herein). The techniques can include recommending one or more exercises, planning for the exercise through a series of guided check-ins and corresponding recommendations both at the time of exercise or several hours beforehand, and guiding and/or monitoring the user through performing the exercise. The techniques can be customized for each user, including based on user preferences (e.g., goals), as well as based on the user's responses to previous exercises.

In one embodiment, the techniques provide a method for recommending one or more types of exercise to a patient with diabetes using a computing device. The method includes receiving, by the computing device, input data indicative of (i) a future exercise start time at which the patient intends to begin exercising and (ii) a present glucose value of the patient. The computing device determines an amount of time between a present time and the future exercise start time. The computing device determines one or more recommended exercise types based on the present glucose value of the patient and the amount of time. The computing device displays, via a display of the computing device, the one or more recommended exercise types.

In one embodiment, the techniques provide a method for recommending, using a computing device, adjustments to treatment for a patient with diabetes based on a planned exercise session. The method includes receiving, by the computing device, input data indicative of (i) a future exercise start time at which the patient intends to begin exercising, (ii) a type of exercise that the patient intends to engage in, and (iii) an initial glucose value of the patient. The computing device displays, via a display of the computing device, an initial recommendation to the user comprising at least one of an adjustment to a planned insulin bolus dose and an adjustment to a planned insulin basal rate, wherein the initial recommendation is based on at least one of the received type of exercise and the received initial glucose value. When a current time is within a first time period of the exercise start time, the computing device prompts a user via the display to provide input indicative of a first scheduled glucose value of the patient. The computing device receives input data indicative of the first scheduled glucose value of the patient. The computing device determines a second recommendation for the patient based on the received first scheduled glucose value. The computing device presents, via the display, the second recommendation.

In one embodiment, the techniques provide a method for customizing a computerized exercise planning tool for developing, using a computing device, an exercise plan for a patient with diabetes. The method includes storing, by the computing device, a set of default rules associated with an exercise planning tool for developing an exercise plan for a patient with diabetes. The computing device receives input data indicative of a user preference for the exercise planning tool. The computing device modifies an aspect of the exercise planning tool, comprising modifying the set of default rules to customize the exercise planning tool for the patient based on the input data. The computing device generates an exercise plan for the patient based on the modified aspect of the exercise planning tool, wherein the exercise plan is different than a second exercise plan that would have been generated using the unmodified set of default rules.

In one embodiment, the techniques provide a method for customizing a computerized exercise planning tool for developing, using a computing device, an exercise plan for a patient with diabetes. The method includes storing, by the computing device, a set of default rules associated with an exercise planning tool for developing an exercise plan for a patient with diabetes. The computing device plans a set of exercise plans for the patient using the exercise planning tool, wherein each exercise plan is associated with an exercise. The computing device monitors data indicative of (i) a treatment aspect of the patient, (ii) a physiological aspect of the patient, or both, for each exercise plan in the set of exercise plans. The computing device modifies the set of default rules to customize the exercise planning tool for the patient based on the monitored data. The computing device generates a new exercise plan for the patient based on the modified set of default rules, wherein the new exercise plan is different than an exercise plan that would have been generated using the unmodified set of default rules.

In one embodiment, the techniques provide a method for providing a recommendation to a patient with diabetes during an exercise using a computing device. The method includes receiving, by the computing device, input data indicative of (i) an exercise being conducted by the patient and (ii) a present glucose value of the patient while conducting the exercise. The computing device determines one or more recommendations based on the present glucose value. The computing device displays, via a display of the computing device, the one or more recommendations.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

FIGS. 5C-5D show tables illustrating exemplary logic that can be used to determine an initial recommendation for a basal adjustment for an aerobic exercise, according to some embodiments.

FIG. 5E shows a table illustrating exemplary logic that can be used to determine an initial recommendation for a bolus adjustment for an aerobic exercise, according to some embodiments.

FIG. 6 shows a table illustrating exemplary logic that can be used to determine and provide an initial recommendation for an anaerobic exercise, according to some embodiments.

FIG. 7C-7E show tables illustrating exemplary logic for determining an initial recommendation for a basal adjustment for a mixed aerobic and anaerobic exercise, according to some embodiments.

FIG. 7F shows a table illustrating exemplary logic for determining a bolus adjustment for a mixed aerobic and anaerobic exercise, according to some embodiments.

FIG. 8A shows an exemplary table illustrating logic that can be used to determine and provide a recommendation for carb intake one hour before an aerobic exercise, according to some embodiments.

FIG. 8B shows an exemplary table illustrating logic that can be used to determine and provide a recommendation one hour before an anaerobic exercise, according to some embodiments.

FIG. 8C shows an exemplary table illustrating logic that can be used to determine and provide a recommendation for carb intake one hour before a mixed aerobic and anaerobic exercise, according to some embodiments.

FIGS. 9A-9D provide examples of a fifteen minute check-in prior to the workout for an aerobic exercise, according to some embodiments.

FIG. 10 provides an example of a fifteen minute check-in prior to the workout for an anaerobic exercise, according to some embodiments.

FIGS. 11A-11C provide examples of a fifteen minute check-in prior to the workout for a mixed aerobic and anaerobic exercise, according to some embodiments.

FIG. 12B shows an exemplary table illustrating logic that can be used to provide a recommendation based on the user's glucose level for anaerobic exercises, according to some embodiments.

FIG. 12C shows an exemplary table illustrating logic that can be used to provide a recommendation based on the user's glucose level for mixed exercises, according to some embodiments.

DETAILED DESCRIPTION

Figure 1:
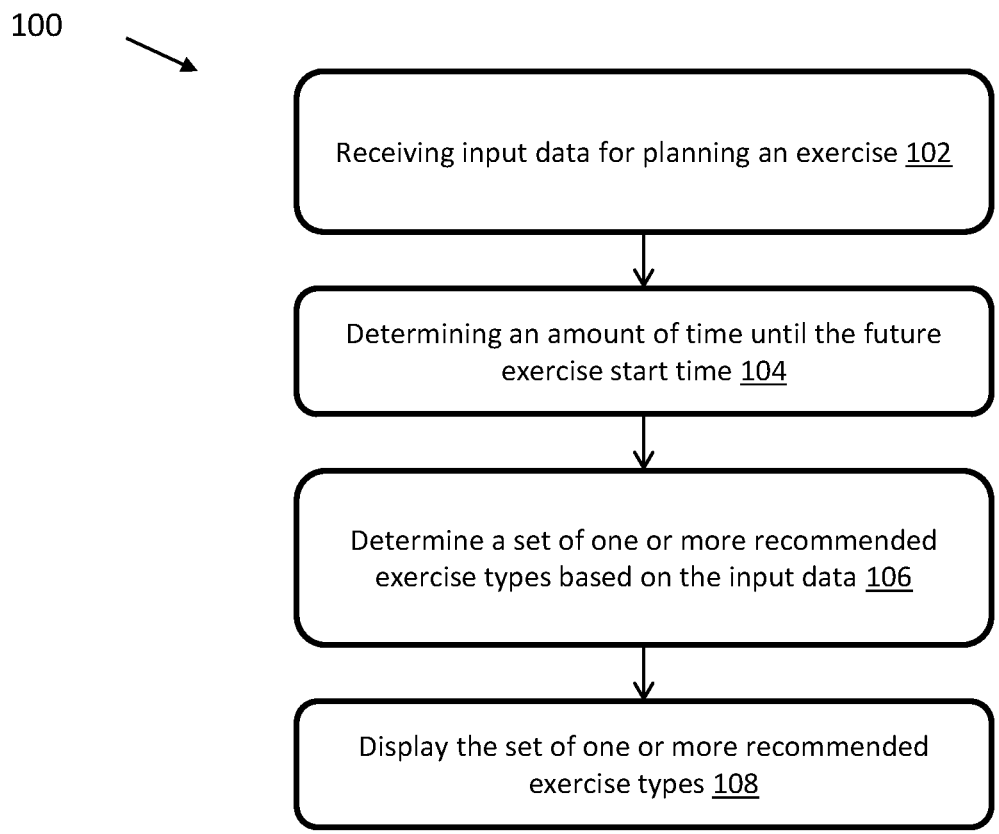
FIG. 1 is an exemplary computerized method for recommending one or more types of exercise to a user, according to some embodiments.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to computer-implemented techniques for planning and performing exercises for diabetic patients. Exercise can be an important part of the lifestyle management of persons with diabetes (e.g., type 1 diabetes) because of, for example, the various cardiometabolic and other benefits it can have for a patient. However, there are challenges in maintaining euglycemia during and after exercise that may complicate safe exercise participation. For example, patients can be at an increased risk of hypoglycemia or hyperglycemia during exercise, hypoglycemia in the 24 hours after exercise, and/or the like.

Guidelines are available to guide persons with diabetes with exercise. However, such guidelines are typically complex and difficult to implement and require individualization to be used effectively.

The techniques described herein provide for computer-implemented techniques (e.g., computer applications, such as mobile phone applications) that provide diabetic patients with the ability to prepare for and conduct a workout. The techniques can adapt otherwise complex and difficult to follow, manual guidelines for exercise, and tailor them to each user, including based on the user's goals, preferences, current metabolic state, personal physiology, past successful treatments, and/or the like. The techniques allow users to plan and/or participate in exercise, while limiting troublesome and sometimes dangerous conditions, such as hypoglycemia and hyperglycemia.

In some embodiments, the techniques can be used to plan anticipated exercises that will occur in the future. In some embodiments, throughout the day the user can interact with the planning tool. For example, the user can provide information regarding current glycemic and insulin status, which the techniques can use to provide tailored recommendations to the user throughout the day, e.g., so that a user can initiate exercise with an optimal glucose level and insulin status to allow participation in the user's preferred form of exercise. Recommendations can be tailored, for example, to the type of exercise (e.g., anaerobic or aerobic), the intensity of the exercise, the duration of the exercise, the user's history and/or monitored historical data, insulin dosing adjustments, carbohydrate supplementation, and/or the like.

In some embodiments, the techniques can be used to identify and/or recommend a preferred activity or activities for exercise based on the user. For example, the system can determine an exercise activity based on a user's glycemic status, insulin status, and/or the like. The system can determine and recommend, based upon the time when the user plans to exercise, the user's current glucose level, and/or the like, particular activities so that the user can undertake an exercise that minimizes glycemic excursions while engaging in the exercise.

In some embodiments, the techniques can be used during an exercise. The techniques can monitor data indicative of current glucose levels, glucose trends, heart-rate, and/or the like while the patient is engaged in exercise to provide notifications of potential interventions during exercise (e.g., in order to limit exercise-related hypoglycemia or hyperglycemia). The techniques can obtain glucose information manually and/or in conjunction with glucose monitoring, such as continuous glucose monitoring (CGM). Examples of such notifications can include changing the type of activity, consuming carbohydrates, taking additional insulin, and/or the like.

In some embodiments, the techniques monitor and analyse the user's history to further customize the techniques for each user. For example, the techniques can include monitoring treatment aspects of the patient (e.g., bolus doses, basal rates, etc.), physiological aspects of the patient (e.g., heart rate, glucose levels, activity data as measured by one or more accelerometers or gyroscopes, etc.), preferred exercise activities, heart rate responses to activities, glycemic responses to types of exercise, how the person feels post-exercise, and/or the like to customize the techniques for each user. The techniques can monitor such aspects of each user's unique history in order to refine future recommendations (e.g., for exercises, exercise planning, etc.). These and other features described herein can work together in a complementary way to allow persons with diabetes to incorporate current best practices and exercise into their lifestyle in a manner that individualizes the guidelines based on a user's unique physiology, preferences, history, and/or the like.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

In some embodiments, the techniques recommend to a user (e.g., to a diabetic patient) what exercises and/or types of exercise(s) to engage in for a planned workout. Generally, as discussed further herein, the device (e.g., a computer, a mobile phone, or other computing device) can request and/or receive information from the user related to planning an exercise, and determine one or more recommended activities that are best-suited for the user based on the input data, the time of the exercise, and/or other relevant information.

FIG. 1 is an exemplary computerized method 100 for recommending one or more types of exercise to a user, according to some embodiments. At step 102, the computing device receives input data for planning an exercise. At step 104, the computing device determines an amount of time until the future exercise start time. At step 106, the computing device determines one or more recommended exercise types based on the user input data. At step 108, the computing device displays, e.g., via a display of the computing device, the one or more recommended exercise types.

Referring to step 102, the input data can include data indicative of a future exercise start time at which the user intends to begin exercising, a present glucose value of the patient, a desired category of exercise, and/or other data relevant for planning an exercise. In some embodiments, the computing device can prompt the user for one or more inputs. For example, the computing device can ask the user when the user plans to work out (e.g., 3 pm later this afternoon, in three hours, etc.). As another example, the computing device can ask the user for the user's current blood glucose reading. In some embodiments, the user is connected to monitoring devices that provide input data to the computing device. For example, the user can be connected to a connected glucose meter (CGM) that provides the user's blood glucose reading to the computing device. In some embodiments, the input data can also include data indicative of an Insulin on Board (IOB) amount for the patient, which can indicate how much active insulin a patient has previously taken and is still circulating through his/her body. The patient's IOB can be used to plan for the exercise. The patient's IOB may be inferred or calculated from previously-taken insulin doses, or the patient may manually input an amount of IOB.

Referring to step 104, the computing device can, for example, determine an amount of time until the future exercise start time by determining the difference between a present time and a future exercise start time received by the user. The computing device can use, for example, an on board clock to determine the time, interface with a timer server, and/or the like. As another example, the computing device can recommend an exercise time, and determine a difference between a present time and the recommended exercise time.

Referring to step 106, the computing device can determine the one or more recommended exercise types based on the user input data, such as based on a present glucose value of the patient, the amount of time until the exercise, a desired type of exercise, the amount of IOB, and/or the like. For example, the computing device can take into consideration how far in the future the patient plans to exercise, and the patient's current blood glucose level to determine the one or more recommended exercises.

Figure 2:
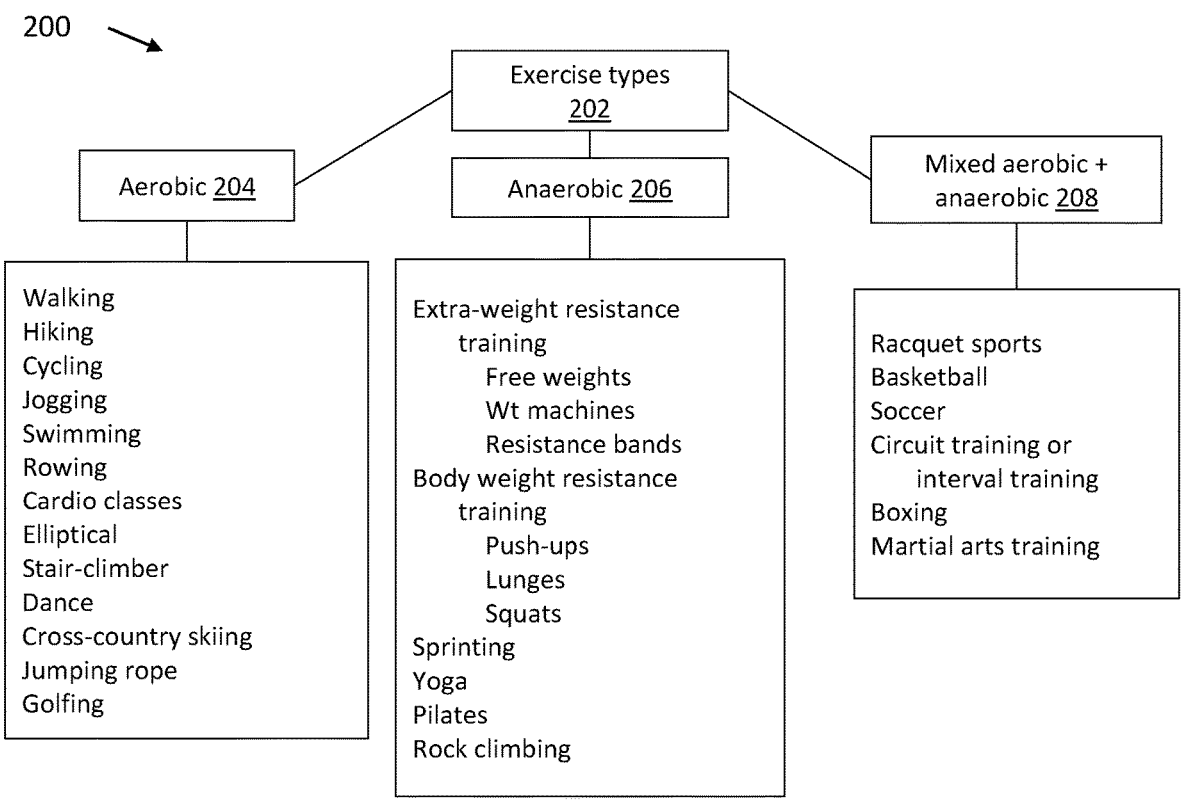
FIG. 2 shows an exemplary grouping of exercise types into aerobic exercises, anaerobic exercises, and mixed aerobic and anaerobic exercises, according to some embodiments.

In some embodiments, the computing device can differentiate between different groups of exercises, store exercises according to different categories, and/or the like. FIG. 2 shows an exemplary grouping 200 of exercise types 202 into aerobic exercises 204, anaerobic exercises 206, and mixed aerobic and anaerobic exercises 208, according to some embodiments. A non-limiting list of exemplary aerobic exercises 204 can include one or more of walking, hiking, cycling, jogging, swimming, rowing, cardio classes, using an elliptical machine, using a stair-climber, dance, cross-country skiing, jumping rope, golfing, and/or the like. A non-limiting list of exemplary anaerobic exercises 206 can include extra-weight resistance training (e.g., free weights, weight machines, resistance bands, and/or the like), body weight resistance training (e.g., push-ups, lunges, squats), sprinting, yoga, pilates, rock climbing, and/or the like. A non-limiting list of exemplary mixed aerobic and anaerobic exercises 208 can include racquet sports, basketball, soccer, circuit training or interval training, boxing, martial arts training, and/or the like.

The computing device can also store, present, consider, or apply criteria for the exercise, a description of the exercise, injection information, tips for the exercise, and/or the like. For example, walking can be categorized or described as a walking at a brisk pace but where the user can still talk while walking. Injection information associated with walking can include a recommendation that an injection be administered in the user's abdomen. Exercise tips for walking can include the tip that walking can drop the user's glucose quickly because there is no adrenaline response, so the user should make sure to bring their hypoglycemic treatment (e.g., glucose tablets, or glucagon) for the walk. Hiking can be categorized or described as walking a long distance across difficult terrain (e.g., in the woods). Injection information associated with hiking can include a recommendation that an injection be administered in either the user's abdomen or arm. Exercise tips for hiking can include: (a) if the user is planning to hike or more than an hour, make sure to bring a hearty snack and water, (b) the user may want to eat a meal (e.g., with a reduced bolus) beforehand, (c) the user should be careful about dropping glucose levels on the way down if the user is hiking a hill or mountain so that the user doesn't trip, and (d) that symptoms may be harder to recognize as the user gets more tired.

Cycling can be categorized or described as stationary, road, track, or trail bicycle-riding. Injection information associated with cycling can include a recommendation that an injection be administered in the arm. Exercise tips for cycling can include the tip to eat a meal with slowly-digested carbs (e.g., and a reduced bolus) before the ride so that the meal will keep the user going. Jogging can be categorized or described as a slow run at a steady pace. Injection information associated with jogging can include a recommendation that an injection be administered in the abdomen. Exercise tips for jogging can include the tip that it is tough to carry food with you while jogging, so think ahead about how to incorporate a hip band or pockets into your athletic gear. Swimming can be categorized or described as laps or other steady, constant activity in the water. Injection information associated with swimming can include a recommendation that an injection be administered in the abdomen. Exercise tips for swimming can include the tip that for frequent swimmers, if the user wears a CGM, the user may want to consider attaching an extra layer of sports or medical tape over the transmitter. Rowing can be categorized or described as the action of propelling forward using boat oars or a machine. Injection information associated with rowing can include a recommendation that an injection be administered in the user's upper backside. Exercise tips for rowing can include the tip that if the user is rowing outdoors, consider getting a waterproof carrier for supplies and hypo treatment.

Cardio classes can be categorized or described as a group classes with a steady, sustained exercise for up to 90 minutes. Injection information associated with cardio classes can include a recommendation that an injection be administered in the user's upper backside. Exercise tips for cardio classes can include the tip that since classes can vary by instructor, to start with a more conservative approach to reducing insulin and/or snacking in preparation for the exercise. Elliptical machine activity can be categorized or described as an activity using an exercise machine like a stationary bike without the seat. Injection information associated with elliptical machine activity can include a recommendation that an injection be administered in the user's arm. Exercise tips for elliptical machine activity can include the tip to make sure the user keeps their foot flat on the pedal to prevent foot or toe numbness while using this machine. The stair climber can be categorized or described as an exercise machine that allows its user to go through motion of climbing stairs at adjustable speeds. Injection information associated with the stair climber can include a recommendation that an injection be administered in the arm. Exercise tips for the stair climber can include the tip to take advantage of a stair climber to create a low-impact workout that burns calories quickly. Dance can be categorized or described as sustained movement to music with many different speeds and styles. Injection information associated with dance can include a recommendation that an injection be administered in the upper backside. Exercise tips for dance can include the tip to choose music and style to improve the user's mood as well as your physical health.

Cross-country skiing can be categorized or described as gliding on skis over relatively flat terrain in ski boots that lift in the back when as the user takes a step. Injection information associated with cross-country skiing can include a recommendation that an injection be administered in the user's arm. Exercise tips for cross-country skiing can include the tip for the user to make sure the user monitors the temperature of their insulin, especially if the user is outside in freezing temperatures. Jumping rope can be categorized or described as leaping over a rope as it is swung around in a sustained, steady pattern. Injection information associated with jumping rope can include a recommendation that an injection be administered in the arm. Exercise tips for jumping rope can include the tip that jumping rope is a great option for exercising in a hotel room or while traveling. Golfing can be categorized or described as a game played on a large, outdoor course involving trying to hit a ball with a club as close as possible to small hole in the group. Injection information associated with golf can include a recommendation that an injection be administered in the upper backside. Exercise tips for golfing can include the tip to try to estimate how many hours the user will be on the course ahead of time to plan snacks accordingly.

Weight-based resistance training can be categorized or described as using extra weight from free weights, a machine, or bands to work specific muscle groups. Injection information associated with weight-based resistance training can include a recommendation that an injection be administered away from muscles the user is targeting. Exercise tips for weight-based resistance training can include the tip that pure anaerobic exercise can make glucose levels rise. Body weight resistance training can be categorized or described as activities like push-ups, lunges, or squats that use one's body weight to challenge certain muscle groups. Injection information associated with body weight resistance training can include a recommendation that an injection be administered away from muscles the user is targeting. Exercise tips for body weight resistance training can include the tip that adding a few of these exercises to a normal aerobic exercise routine can help to stabilize glucose levels and make the routine both aerobic and anaerobic. Sprinting can be categorized or described as running as fast as one can for 400 m or less. Injection information associated with sprinting can include a recommendation that an injection be administered in the upper backside. Exercise tips for sprinting can include the tips (a) if the sprinting turns into jogging, glucose levels are likely to drop, and (b) anaerobic sprints should stay as short bursts of intense running.

Yoga can be categorized or described as attempting a variety of bodily postures and mindful breathing to build strength and flexibility. Injection information associated with yoga can include a recommendation that an injection be administered in any site. Exercise tips for yoga can include the tip that if the user is attending a hot yoga class, remember to hydrate and eat a small meal before class to avoid nausea. Pilates can be categorized or described as exercises, sometimes using special equipment, focused on strength and flexibility of the core muscles. Injection information associated with pilates can include a recommendation that an injection be administered in the arm or leg. Exercise tips for pilates can include the tip that if the user is doing Pilates on a mat, consider attaching your CGM and/or infusion site to a location that will be comfortable while lying on the floor. Rock climbing can be categorized or described as using one's hands and feet to ascend a series of rock steps (e.g., indoor or outdoor). Injection information associated with rock climbing can include a recommendation that an injection be administered in the upper backside. Exercise tips for rock climbing can include the tip to consider taking a fingerstick glucose level check immediately before climbing. Racquet sports can be categorized or described as tennis, racquetball, squash, etc., that involve short bursts of sprinting and steadier movement through the course of a game. Injection information associated with racquet sports can include a recommendation that an injection be administered in the upper backside. Exercise tips for racquet sports can include the tip that if the user has a particularly intense game, the user may not see the glucose-lowering effects of the aerobic exercise.

Basketball can be categorized or described as sustained jogging and sprinting while shooting a ball at the opponent's basket. Injection information associated with basketball can include a recommendation that an injection be administered in the user's upper backside. Exercise tips for basketball can include the tip to keep in mind that there may be different glycemic effects to playing indoors versus outdoors. Soccer can be categorized or described as a game with sustained running that involves kicking a ball into the opponent's goal. Injection information associated with soccer can include a recommendation that an injection be administered in the user's arm. Exercise tips for soccer can include the tip to be aware of varying glycemic effects when the user plays on grass, sand, pavement, etc.

Circuit training or interval training can be categorized or described as completing a series of high-intensity exercises for 30 seconds to 5 mins each. Injection information associated with circuit training or interval training can include a recommendation that an injection be administered in any site. Exercise tips for circuit training or interval training can include the tip for the user to stagger aerobic with anaerobic activities to help to keep glucose levels stable. Boxing can be categorized or described as a sport involving attack and defense using one's fists. Injection information associated with boxing can include a recommendation that an injection be administered in the leg or upper backside. Exercise tips for boxing can include the tip to take note of the differences in glucose levels between training and sparring, since because of the adrenaline involved in sparring, the user's levels may go up. Martial arts training can be categorized or described as several disciplines of attack and defense. Injection information associated with martial arts training can include a recommendation that an injection be administered in any site. Exercise tips for martial arts can include the tip that if the user's class is in the evening, consider eating a snack before bed to prevent overnight hypoglycemia.

Referring back to step 106 in FIG. 1, the computing device can be configured to recommend one or more exercises based on the amount of time determined at step 104, the user input data from step 102, and/or some combination thereof. In some embodiments, the computing device can be configured to determine the one or more exercises to recommend based on a threshold amount of time. For example, if the user plans to work out beyond a threshold amount of time (e.g., greater than one hour from the current time), the computing device may recommend a first set of one or more exercise types from a first category of exercises as well as a second set of one or more exercises from a second category of exercises. In some embodiments, the computing device may also optionally recommend a third set of one or more exercise types from a third category of exercises in addition to the first set and the second set of exercise types. In some embodiments, the first category of exercises can be aerobic exercises, the second category of exercises can be anaerobic exercises, and the optional third category of exercises can be mixed aerobic and anaerobic exercises. The computing device may also consider and/or recommend other categories of exercises, as discussed further herein, such as further-refined categories determined based on the user's previous exercise activities).

While the techniques can be configured to accommodate a user's exercise preference, if depending on the time (e.g., as exercise time approaches) the desired exercise is not a safe choice, the techniques can be configured to provide the user with one or more alternative exercises. For example, if the user plans to work out at a time that does not meet the threshold amount of time (e.g., if the user plans to work out less than or equal to one hour from the current time), the computing device can present different exercises based on the users blood glucose (BG) reading. In some embodiments, the system can use one or more thresholds for determining which exercise(s) to recommend to the user. For example, if the user's glucose is less than a first threshold, the computing device can be configured to provide exercises from a first category, and if the user's glucose is greater than or equal to the first threshold, the computing device can be configured to provide exercises from a second (different) category. In some embodiments, the first threshold is in the range between 130 mg/dL and 160 mg/dL, 140 mg/dL and 150 mg/dL, and/or the like.

In some embodiments, the computing device can use one or more ranges between thresholds for determining which exercise(s) to recommend to the user. For example, if the user's glucose is between a first range of thresholds (e.g., between 144 mg/dL-350 mg/dL), the computing device can recommend one or more aerobic exercises. As another example, if the user's glucose is between a second range of thresholds (e.g., between 90 mg/dL-144 mg/dL), the computing device can recommend one or more anaerobic exercises. As a further example, if the user's glucose is between a third range of thresholds (e.g., between 100 mg/dL-160 mg/dL), the computing device can recommend one or more mixed aerobic and anaerobic exercises. As another example, the lower threshold for a range of thresholds can be a value from the range of 80 mg/dL to 120 mg/dL, from the range of 95 mg/dL to 105 mg/dL, and/or the like. The higher threshold for the range of thresholds can be a value from 140 mg/dL to 180 mg/dL, 155 mg/dL to 165 mg/dL, and/or the like.

At step 108, the computing device can present the user with the one or more determined exercises. For example, the computing device can present the user with a menu of recommended types of physical exercise. The user can then select or otherwise input a type of physical exercise that the user intends to engage in for planning using the techniques discussed herein. In some embodiments, the computing device may provide one or more safety responses (e.g., instead of, or in addition to, an exercise). For example, if the user's glucose is less than or equal to 50 mg/dL, the computing device may determine that the user's glucose is too low (e.g., the user is in severe hypoglycemia). The computing device may not present any exercises and/or can present a cautionary message. For example, the computing device can warn the user to take caution because their glucose level is too low for safe physical activity, and that the user should treat immediately with fast-acting glucose or glucagon as advised by their health care professional. As another example, if the user's glucose is greater than or equal to 270 mg/dL, the computing device may not present any exercises, and/or can present a cautionary message. For example, the computing device can request that the user check for ketones, and if they are not present or if there is only a low concentration, then mild exercise can begin, otherwise if the user has an elevated ketone concentration, then the user should follow the procedure advised by their health care professional. As another example, if the user cannot perform ketone testing, then the user can take time to correct their high glucose level (e.g., as advised by their health care professional) and reschedule the desired exercise activity. The computing device can set a reminder for the user to recheck their glucose level in the future (e.g., 15, 30, or 60 minutes) to continue with exercise recommendation and/or planning.

Figure 3A:
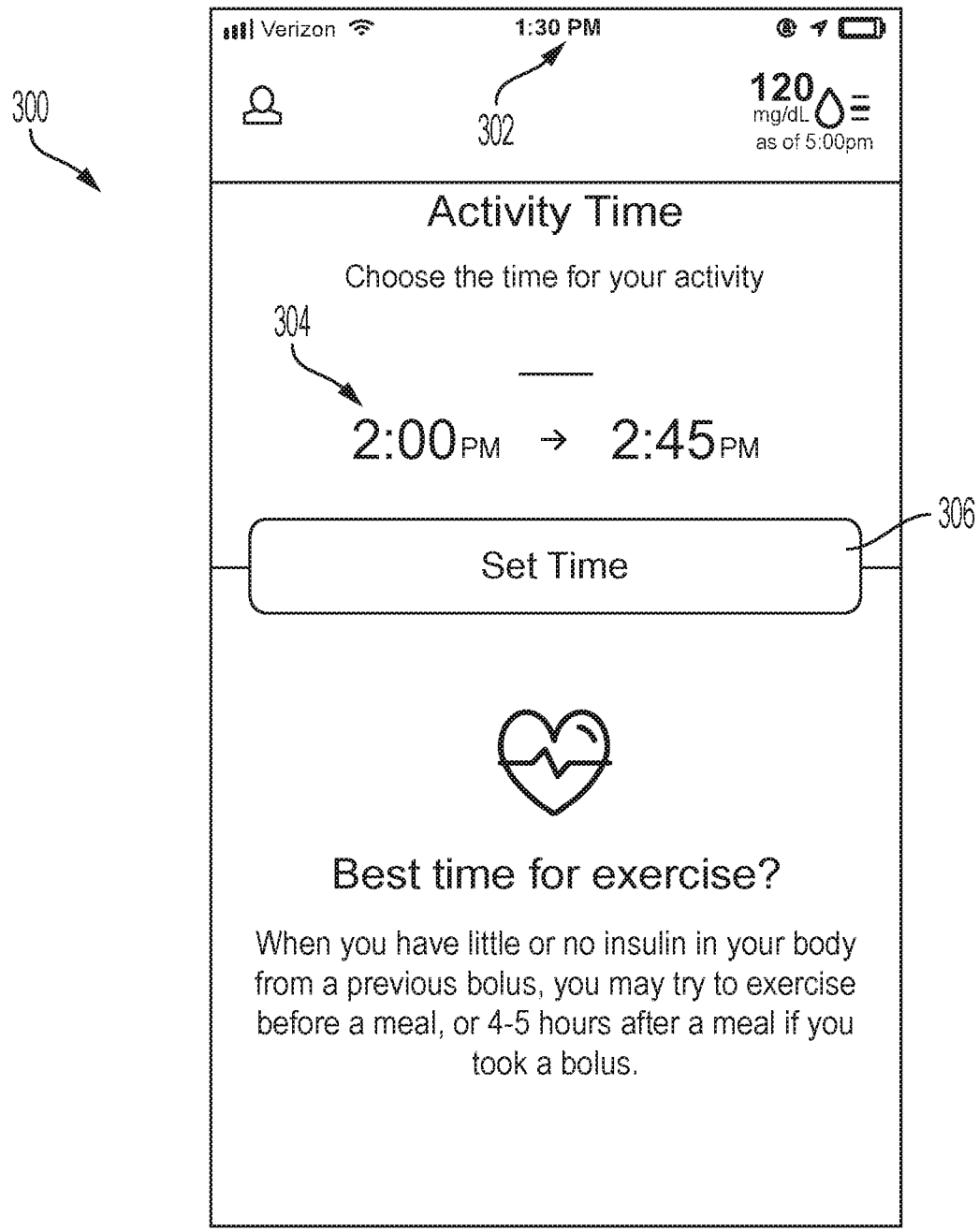
FIGS. 3A-3I show a series of exemplary screenshots shown on the display of the computing device, according to some embodiments.
Figure 3B:
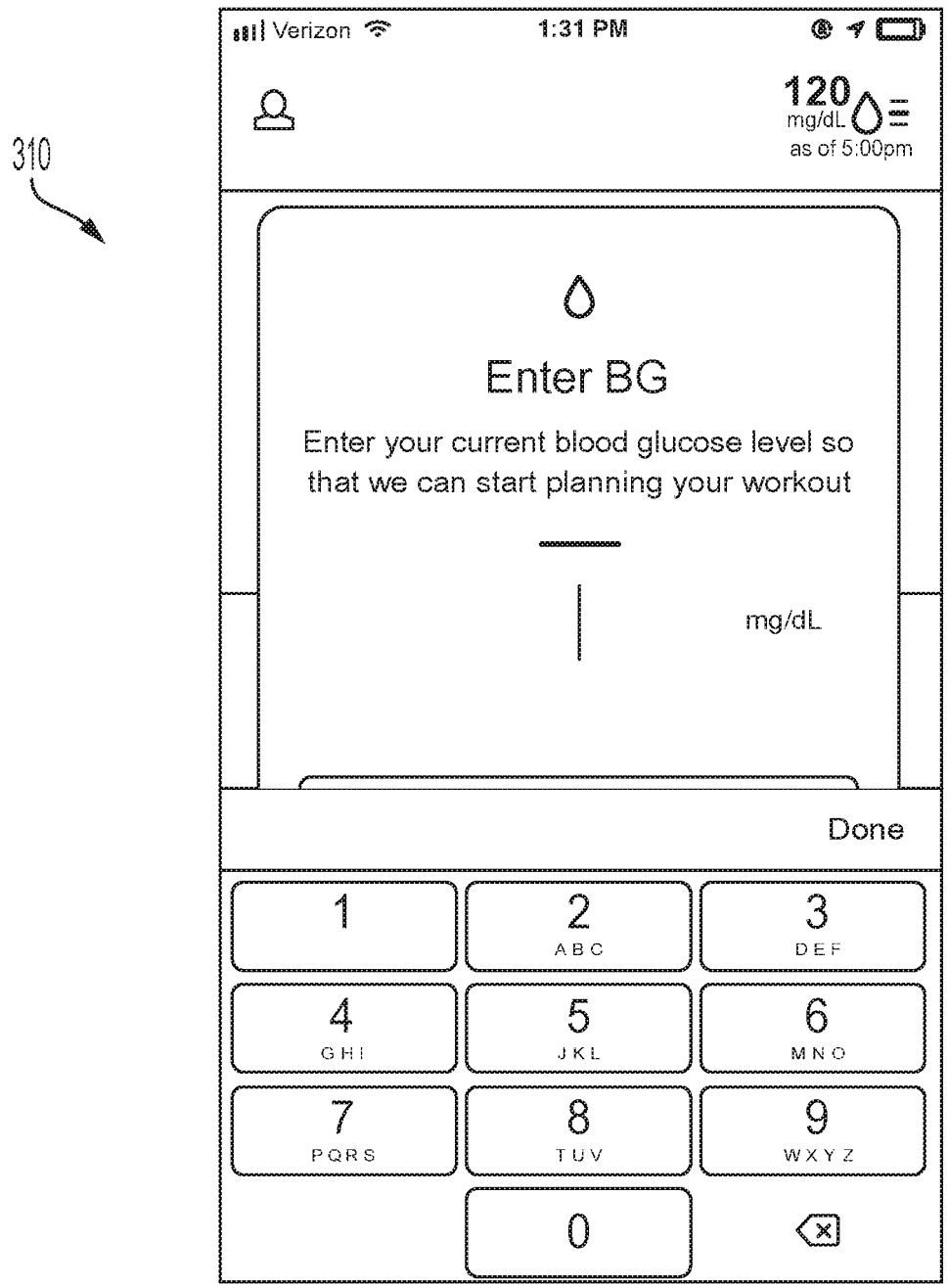
Figure 3C:
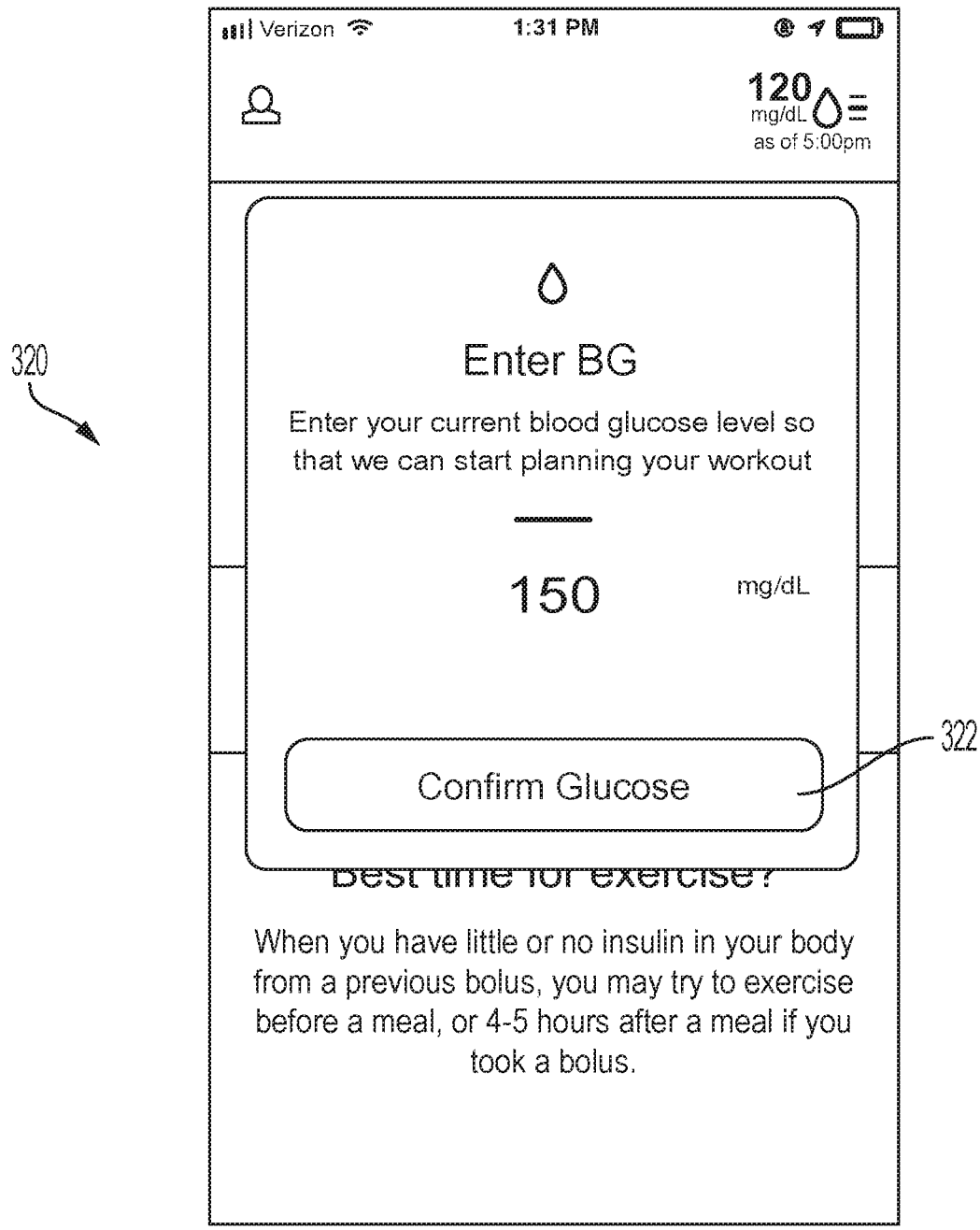

FIGS. 3A-3I show a series of exemplary screenshots of the display of the computing device (e.g., a mobile application, in this example), according to some embodiments. FIG. 3A shows an exemplary display 300 prompting a user to schedule their activity. The current time 302 is 1:30 PM, and the patient has scheduled an exercise session for 2:00 pm-2:45 pm, as shown at 304. The patient can select the "Set Time" button 306, which causes the computing device to transition to the display 310 shown in FIG. 3B. The display 310 prompts the user to enter their current glucose level. As discussed herein, in some embodiments, if the user is wearing a CGM, then screen 310 may be omitted (e.g., since the user's glucose level can be provided automatically). FIG. 3C shows display 320, requesting the user to press button "Confirm Glucose" 322 for the user to confirm the current glucose level of 150 mg/dL (e.g., which the user entered using display 310, or which was received from a CGM).

Figure 3D:
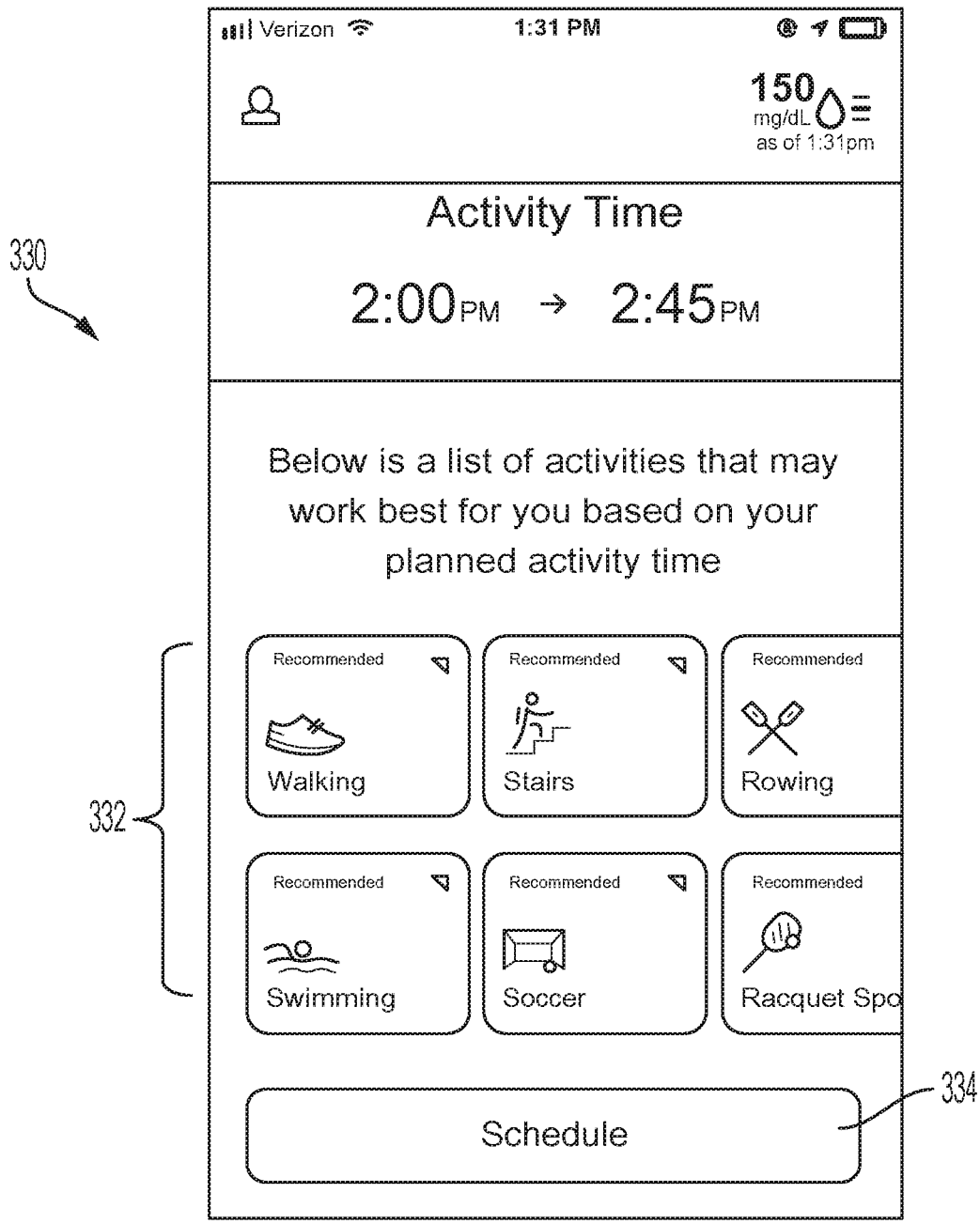
Figure 3E:
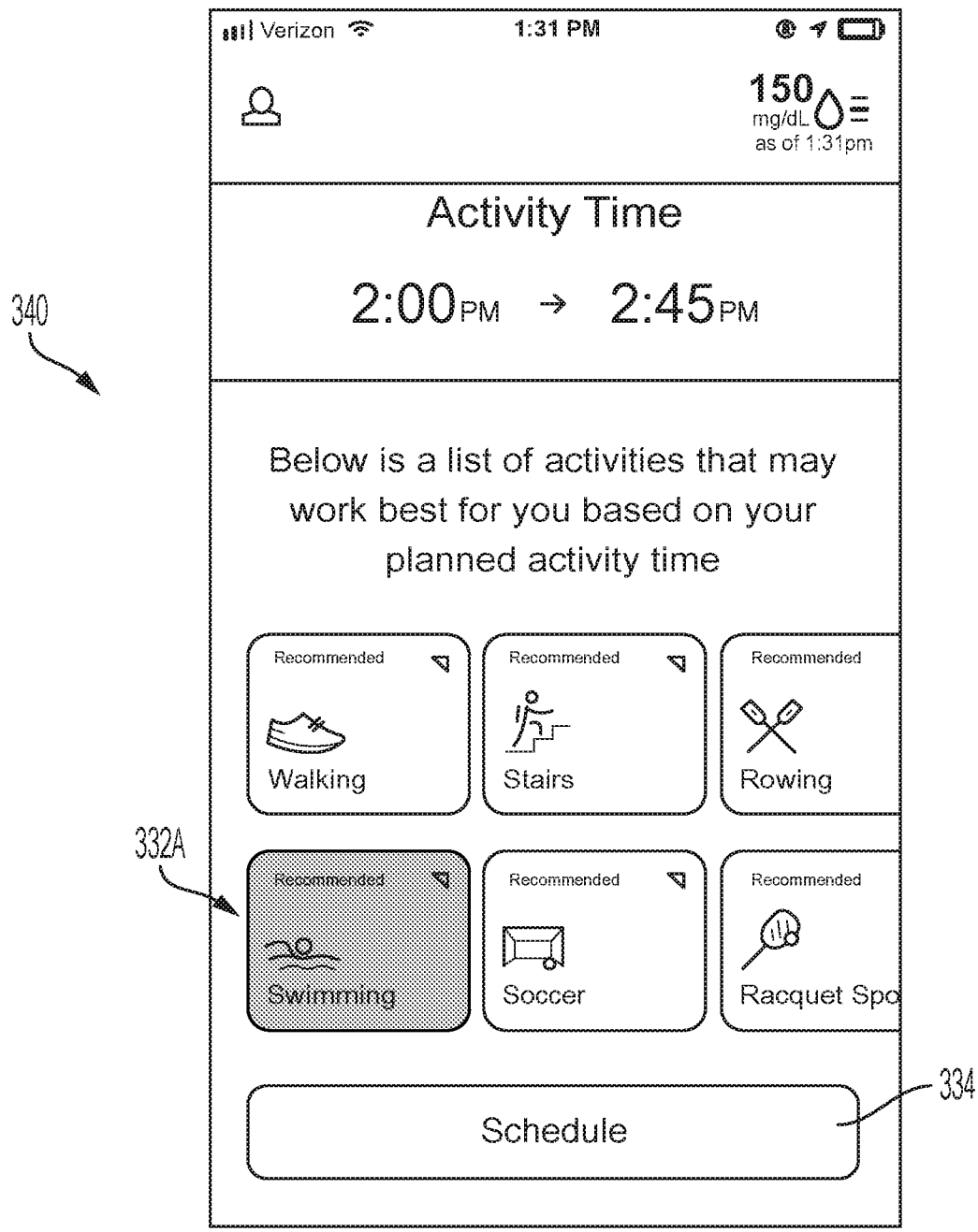
Figure 3F:
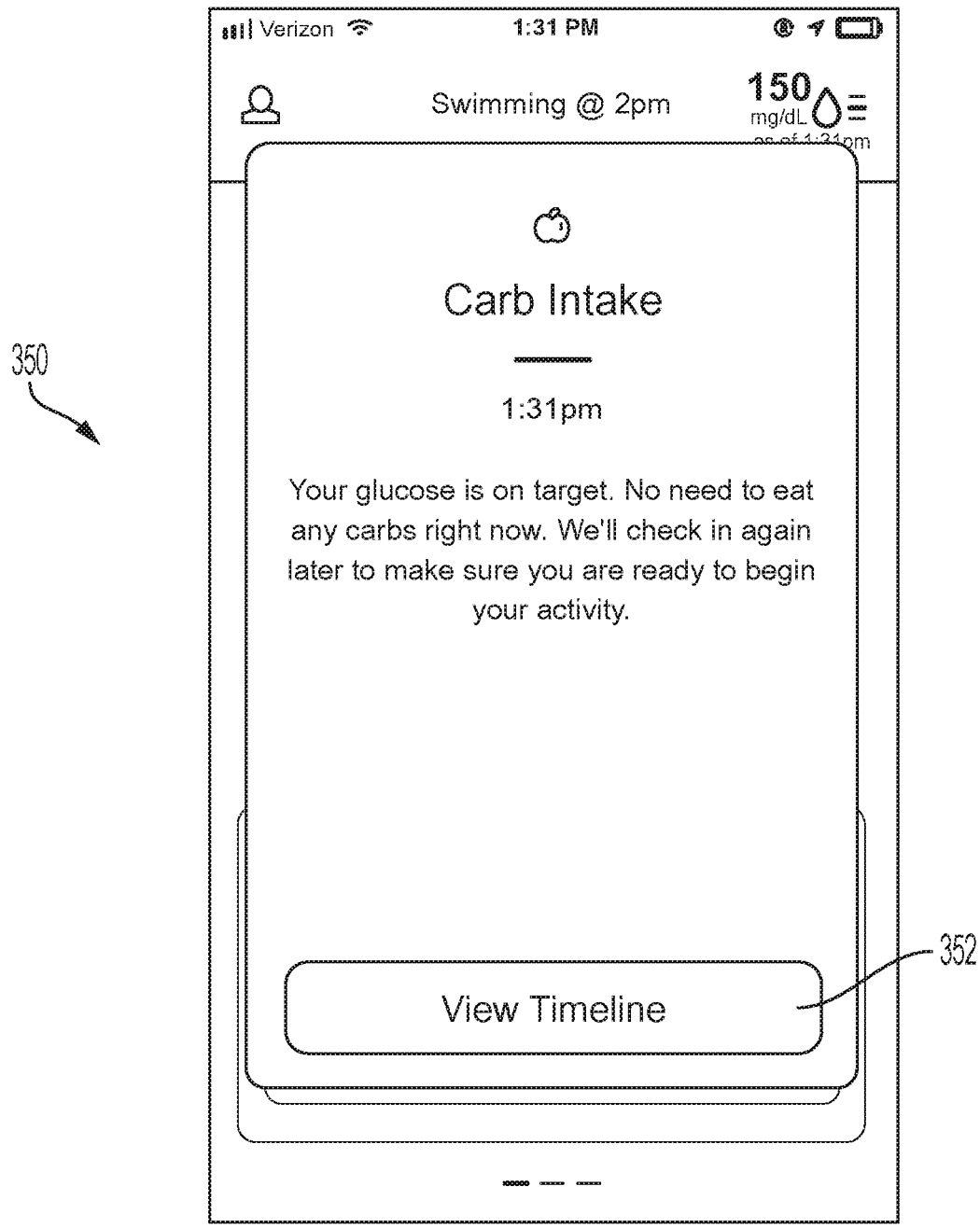
Figure 3G:
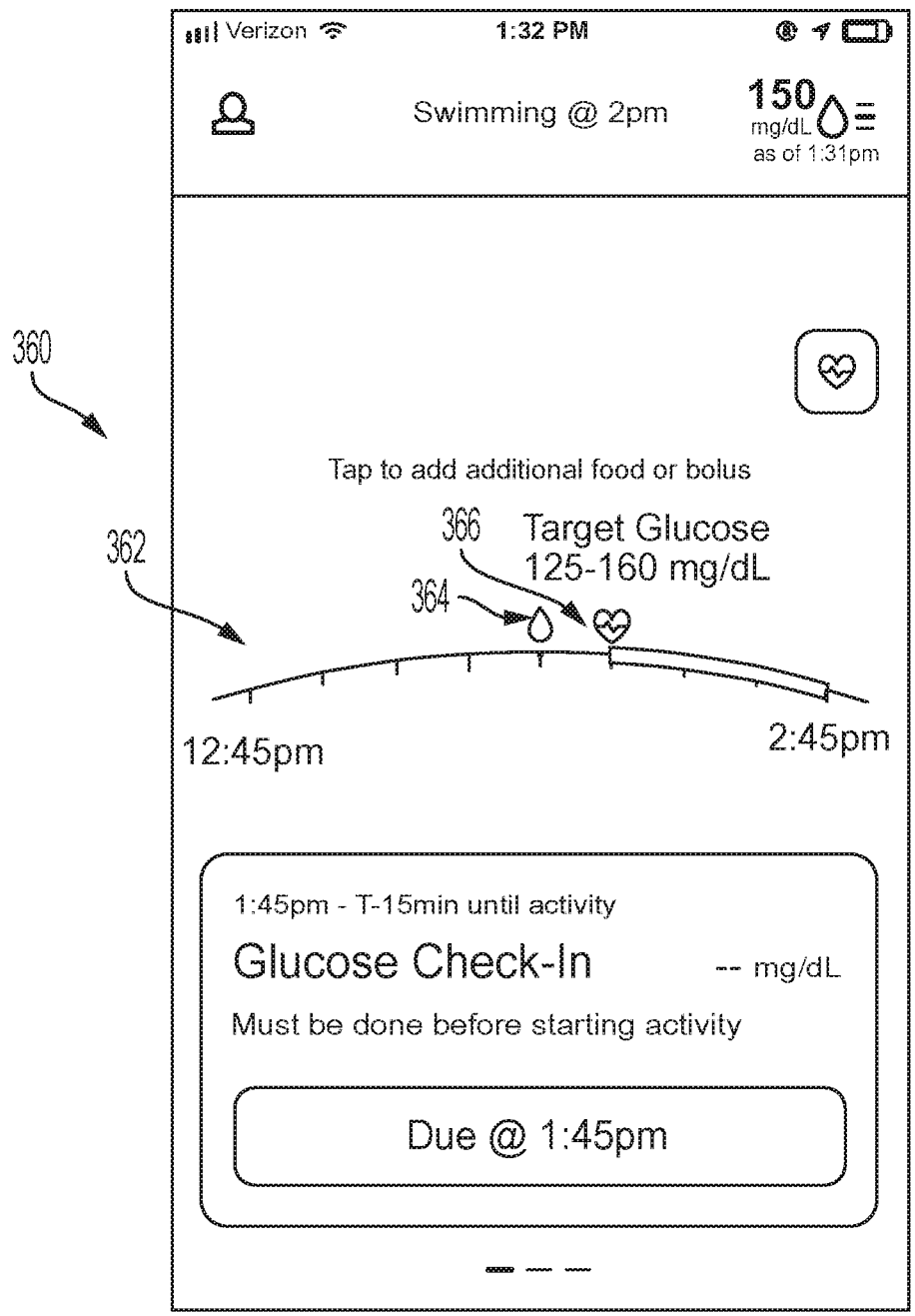

After confirming the glucose level using screen 320, the user is presented with screen 330 shown in FIG. 3D. Screen 330 allows the patient to choose a type of exercise. Screen 330 can present, for example, the one or more exercises determined using the computerized method 100 discussed in conjunction with FIG. 1. In this example, since only six exercises 332 are presented to the user in display 330, the user can scroll to reveal more types of exercises (e.g., if the system determines more than six exercises for the user). As discussed herein, the types of exercises presented can vary, e.g., depending on how soon the patient plans to work out, the patient's current glucose level, and/or the like. The "Schedule" button 334 is not available (e.g., is grayed out) because the user has not selected an exercise 332. FIG. 3E shows display 340, in which exercise 332A (swimming) is highlighted because the user selected exercise 332A. The "Schedule" button 334 can now be selected by the user, which, upon selection, selects exercise 332A for planning, as discussed further herein.

In some embodiments, the techniques can check-in with a user at one or more time points (e.g., upon scheduling the exercise, 1 hour before the scheduled exercise, 15 minutes before the scheduled exercise, 15 minutes after the scheduled exercise, and/or the like) to guide the user in preparation for and/or after completion of the exercise. At each checkpoint, the user can provide data, such as a glucose level at each checkpoint. The system can use the input data to make one or more recommendations to the user, such as recommendations to consume foods, to adjust a bolus rate, a basal amount, and/or the like. The recommendations provided to the user can change dynamically throughout the day based on the user check-ins. For example, as explained further herein, if a user initially plans to run five miles at 5:00 pm, if at 5:00 pm the user likely cannot run five miles safely, the techniques can indicate that the user undertakes other activities. As another example, the results of one check-in may influence the recommendations provided in response to that check-in and/or recommendations for other check-ins.

Figure 4:
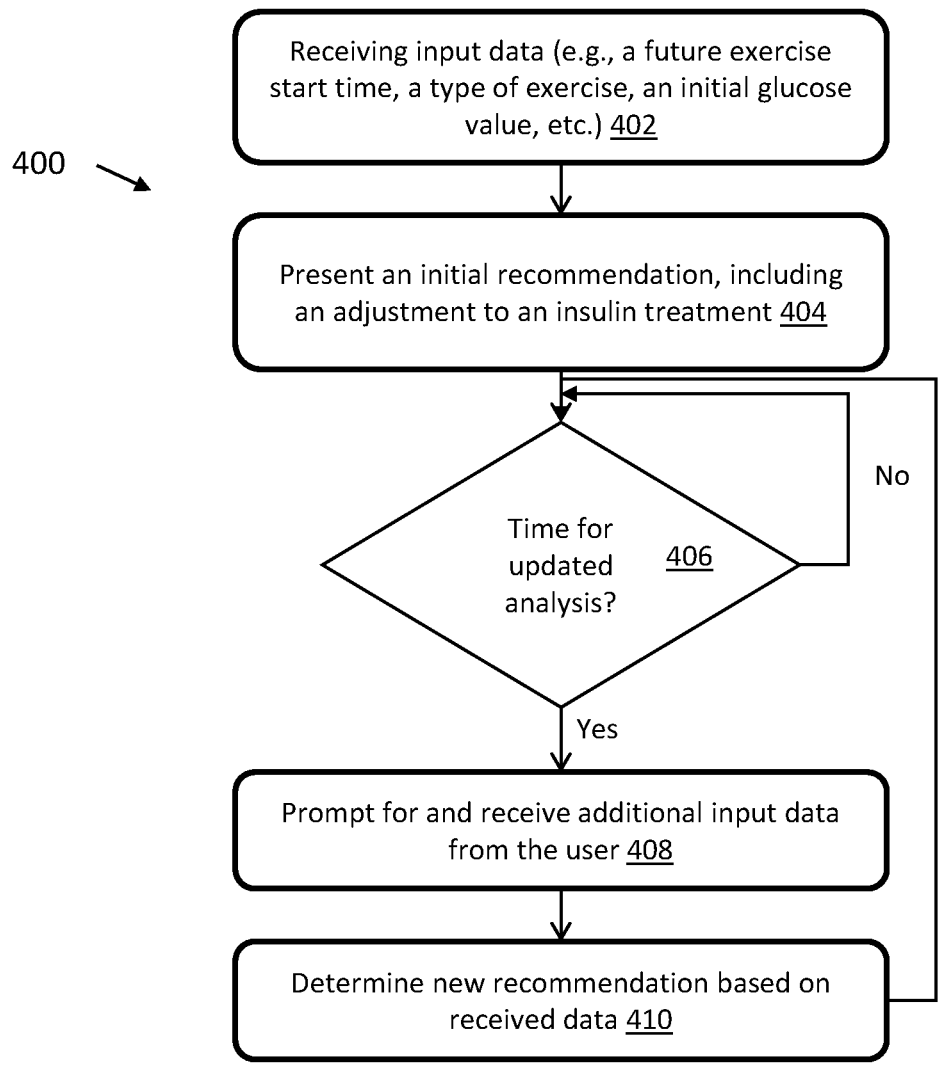
FIG. 4 shows an exemplary computerized method for checking in with a user at one or more time periods, according to some embodiments.

FIG. 4 shows an exemplary computerized method 400 for checking in with a user at one or more time periods for providing one or more recommendations for planning an exercise, according to some embodiments. At step 402, the computing device receives input data for planning the exercise (e.g., a future exercise start time, a type of exercise, and/or an initial glucose value, according to the techniques discussed herein). At step 404, the computing device presents, via a display of the computing device, an initial recommendation to the user. At step 406, the computing device determines whether it is time for performing an updated analysis for the exercise (e.g., such as to determine whether to display any further recommendations). If it is time to perform an updated analysis, the method 400 proceeds to step 408, otherwise the method 400 waits until it performs another time check. At step 408, the computing device prompts the user for, and receives, additional input data from the user. At step 410, the computing device determines a second recommendation for the patient based on the received additional input data (e.g., which the computing device presents to the user via the display). The method 400 can proceed back to step 406 to provide additional check-in(s).

The method 400 can be used to provide one or more planned recommendations, such that the user can plan an exercise activity for later in the day (e.g., after work) and the computing device (e.g., phone application) can guide the user throughout the day with multiple glucose level check-ins and recommendations (e.g., for adjusting boluses or basal rate, ingesting carbs, etc.) at multiple time points leading up to the exercise activity, during the exercise activity, and/or after the exercise activity. As discussed herein, the recommendations can be tailored based on exercise, time, the user's goals, and/or the like. For example, depending on certain time periods before the exercise, the computing device can check in with the user and request further information to provide additional recommendations. As also discussed further herein, the recommendations can be used to provide iterative adjustments. For example, as a user's glucose levels fluctuate, the computing device can adjust its recommendations at check-ins to keep the user on track for a target range for the time of exercise. As described further herein, the techniques can recommend specific activities within either the aerobic, anaerobic, or mixed types of exercises to accommodate the glucose level at the time of activity start.

Referring to step 402, the input data can include data indicative of a future exercise start time at which the patient intends to begin exercising, a type of exercise that the patient intends to engage in, an initial glucose value of the patient, and/or the like. In some embodiments, the computing system receives some (or all) of the input data when determining which exercise the user is going to perform, such as discussed in conjunction with method 100 in FIG. 1. Therefore, in some embodiments, the computing device may have already received some data and therefore does not need to obtain that data again (e.g., as long as the data is still current).

Referring to step 404, the initial recommendation can include an adjustment to a planned insulin bolus dose, an adjustment to a planned insulin basal rate, a recommendation to eat carbs, and/or other recommendations. In some embodiments, the computing device determines the initial recommendation based on the type of exercise, the user's initial glucose value, and/or the like. In some embodiments, the initial recommendation is determined upon scheduling the exercise.

Figure 5A:
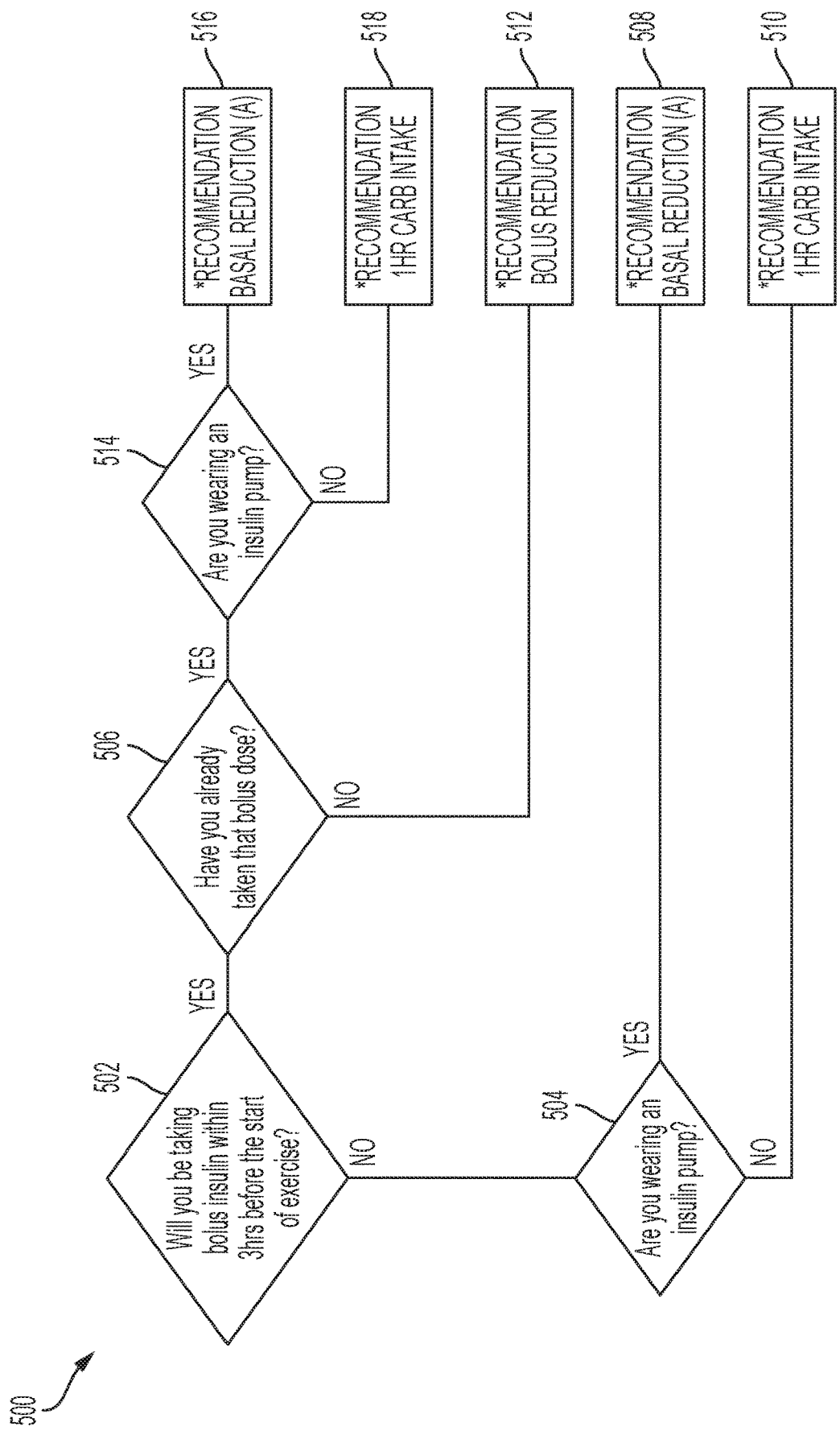
FIGS. 5A-5B shows an exemplary computerized method for providing an initial recommendation for an aerobic exercise, according to some embodiments.
Figure 5B:
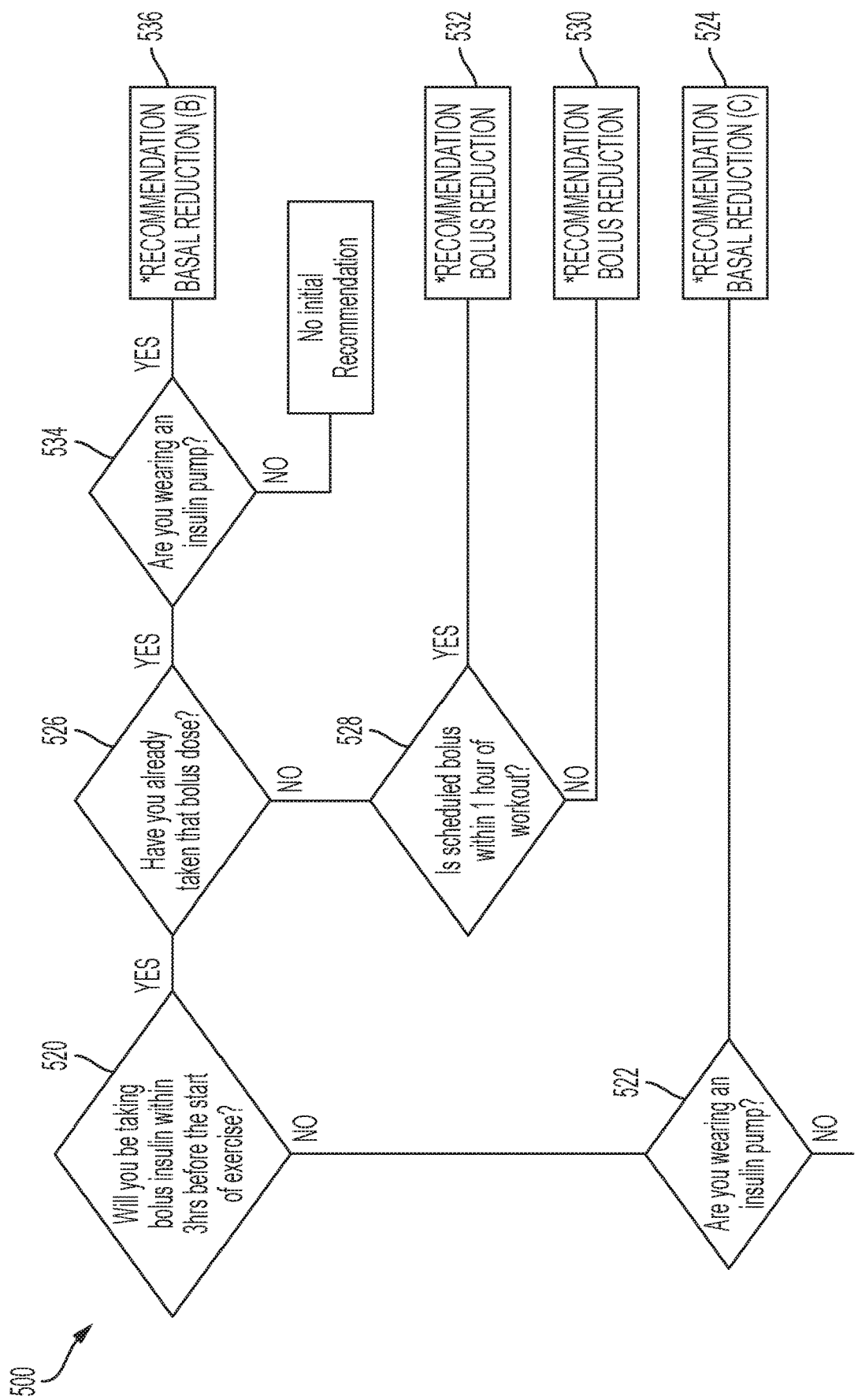

FIGS. 5A-5B shows an exemplary computerized method 500 for providing an initial recommendation for an aerobic exercise, according to some embodiments. Where the discussion below refers to the computerized method 500 or a computing device "determining" a fact, a quantity, or some other piece of data, this determination may be made by prompting the user with a query and receiving user input in response to the query. In some cases, this determination may also be made by consulting, by the computerized method or a computing device, pre-stored parameters or rules regarding a user's preferences or treatment regimen. In some cases, this determination may by a computing device by communicating with an external sensor or device, such as a CGM sensor or an on-body infusion pump worn by the user. In some cases, this determination may also be based at least partly on a log of patient treatment or physiological data, e.g., a record of the user's recent glucose levels or insulin doses.

If, for example, the exercise is scheduled within a threshold time period of the exercise (e.g., within one hour), the method 500 starts at step 502 in FIG. 5A. At step 502, the computing device determines whether the user will be taking bolus insulin within three hours before the start of the exercise. If no, the method proceeds to step 504, otherwise the method proceeds to step 506. At step 504, the computing device determines whether the user is wearing an insulin pump. If yes, the method proceeds to step 508 and provides a recommendation for a basal reduction (A), discussed further herein in conjunction with FIG. 5C. If no, the method proceeds to step 510 and provides a recommendation for carb intake.

Turning back to step 506, if the user has not already taken the bolus dose, the method proceeds to step 512 and provides a recommendation for a bolus reduction, as discussed further in conjunction with FIG. 5E. If the user has already taken the bolus dose, the method proceeds to step 514 and determines if the user is wearing an insulin pump. If the user is wearing an insulin pump, the method proceeds to step 516 and recommends a basal reduction (A). If the user is not wearing an insulin pump, the method proceeds to step 518 and recommends a carb intake.

If, for example, the exercise is not scheduled within a threshold time period of the exercise (e.g., within one hour), the method 500 starts at step 520 in FIG. 5B. At step 520, the computing device determines whether the user will be taking a bolus insulin within three hours before the start of exercise. If no, the method proceeds to step 522 and determines whether the user is wearing an insulin pump. If no, then the method does not provide an initial recommendation. Otherwise, the method proceeds to step 524 and recommends a basal reduction (C) discussed further in conjunction with FIG. 5D. Turning back to step 520, if yes, the method proceeds to step 526 and determines whether the user already took the bolus dose. If no, the method proceeds to step 528 and determines if the user has a scheduled bolus within 1 hour of the workout. If no, the method proceeds to step 530 and recommends a bolus reduction. If yes, the method proceeds to step 532 and recommends a bolus reduction (e.g., which may vary depending on the amount of time to the exercise, as discussed in conjunction with FIG. 5E). Referring back to step 526, if the user already took the bolus dose, at step 534 the system checks or determines whether the user is wearing an insulin pump. For example, the patient may have provided the computing device with information indicative of whether the patient is wearing an insulin pump, and/or the computing device can request such information from the user. If no, the computing device provides no initial recommendation. If yes, the computing device proceeds to step 536 and recommends a basal reduction (B), discussed further in conjunction with FIG. 5D.

Figure 5D:
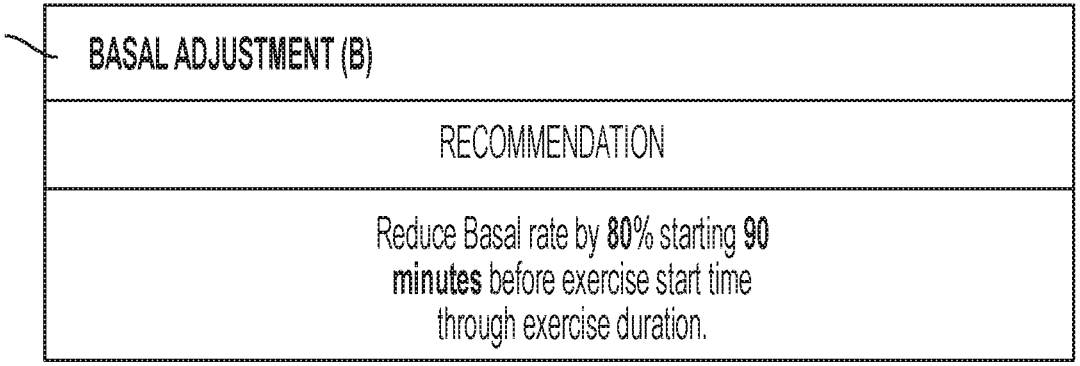
Figure 5D:
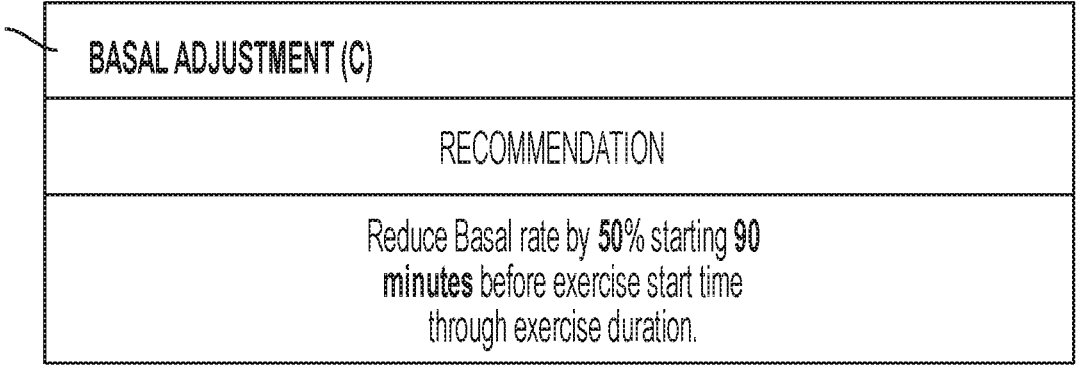

FIG. 5C shows a table 540 showing exemplary logic that can be used to determine an initial recommendation for a basal adjustment (A), which is determined based on the glucose 542 of the user to provide an associated recommendation 544. For example, if the user's glucose is less than or equal to 90 mg/dL, the computing device provides an initial recommendation to consume 16 g of glucose tabs and to reduce basal rate by 80% starting now through the exercise duration. FIG. 5D shows a table 560 showing exemplary logic that can be used to determine shows a basal adjustment (B) and a table 570 showing exemplary logic that can be used to a determine basal adjustment (C). FIG. 5E shows a table 580 showing exemplary logic that can be used to determine a bolus adjustment determined based on the exercise intensity 582 and whether the exercise is within 30-60 minutes (584), or more than 60 minutes (586) from the current time.

In some embodiments, the computing device is configured to determine and provide an initial recommendation for an anaerobic exercise. For example, the computing device can determine and provide a recommendation using the exemplary logic shown in the table 600 in FIG. 6. The computing device can determine the recommendation based on the user's glucose reading 602 and whether the user is (604) or is not (606) wearing an insulin pump. For example, if the user's glucose is between 151-250 mg/dL, and the user is wearing a pump, then the computing device recommends to temporarily increase the user's basal rate by 20% until the user's glucose is between 120-150 mg/dL, otherwise if the user is not wearing a pump the computing device does not provide a recommendation.

Figure 7A:
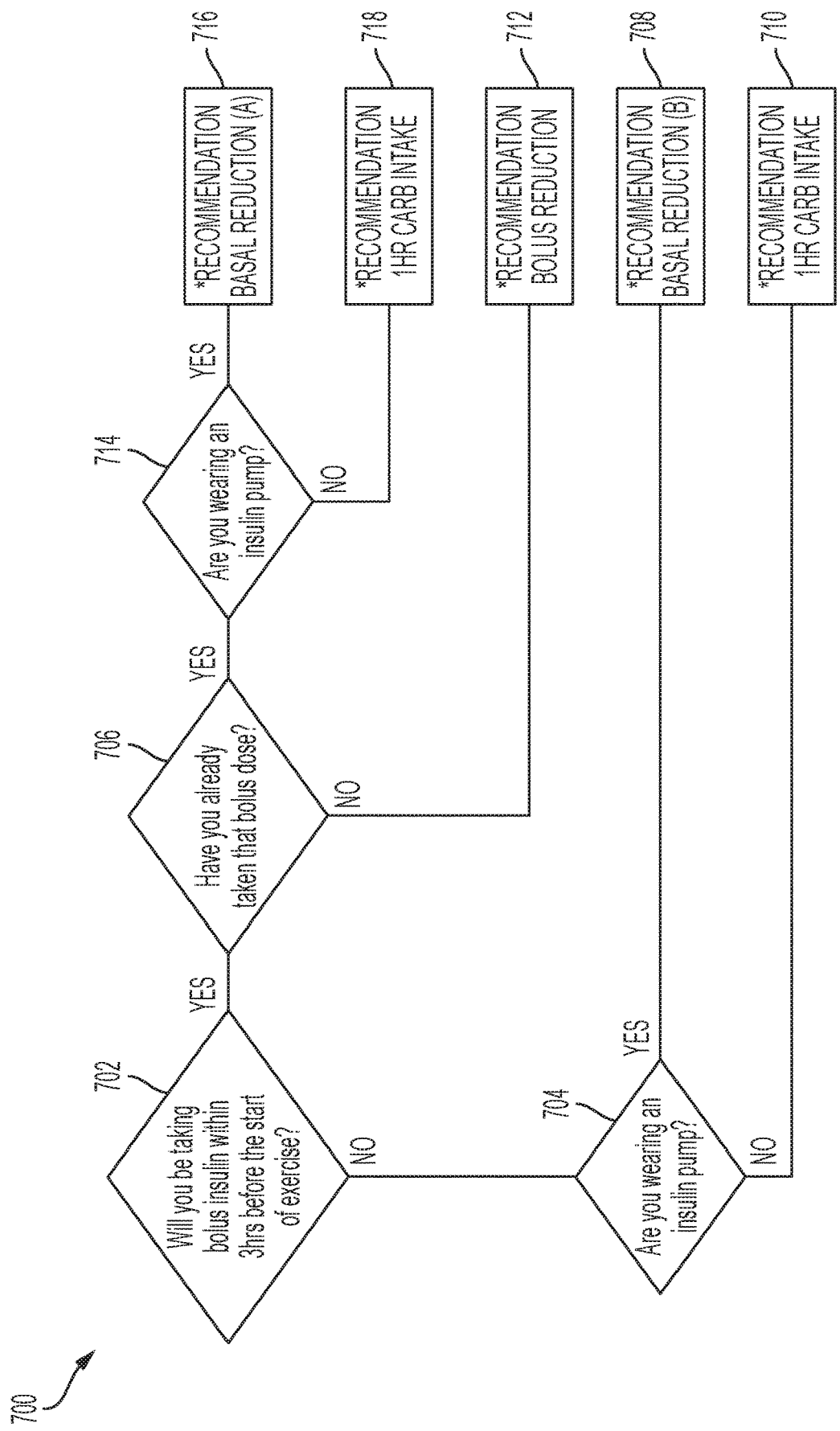
FIGS. 7A-7B show an exemplary computerized method for providing an initial recommendation for a mixed aerobic and anaerobic exercise, according to some embodiments.
Figure 7B:
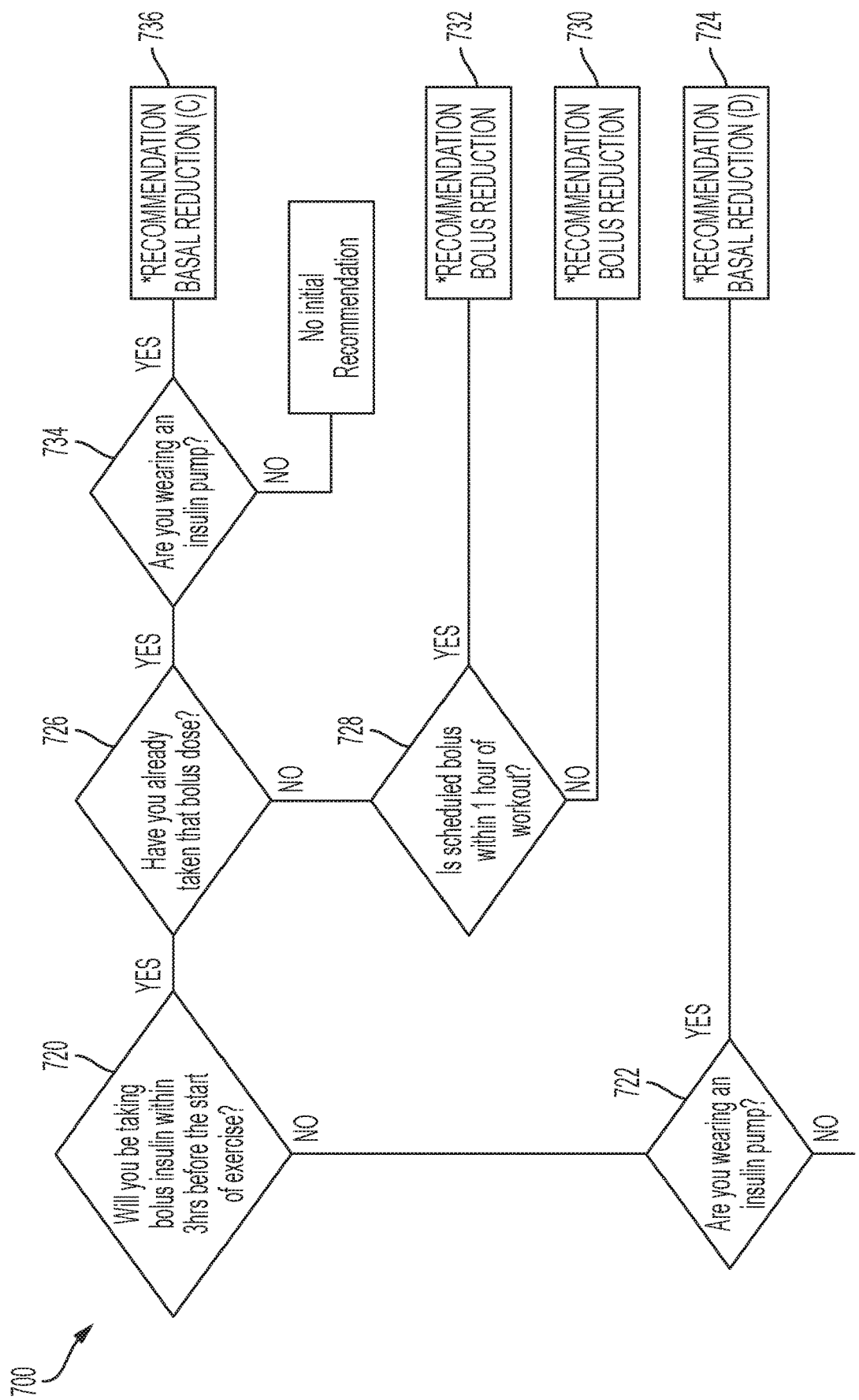
Figure 9A:
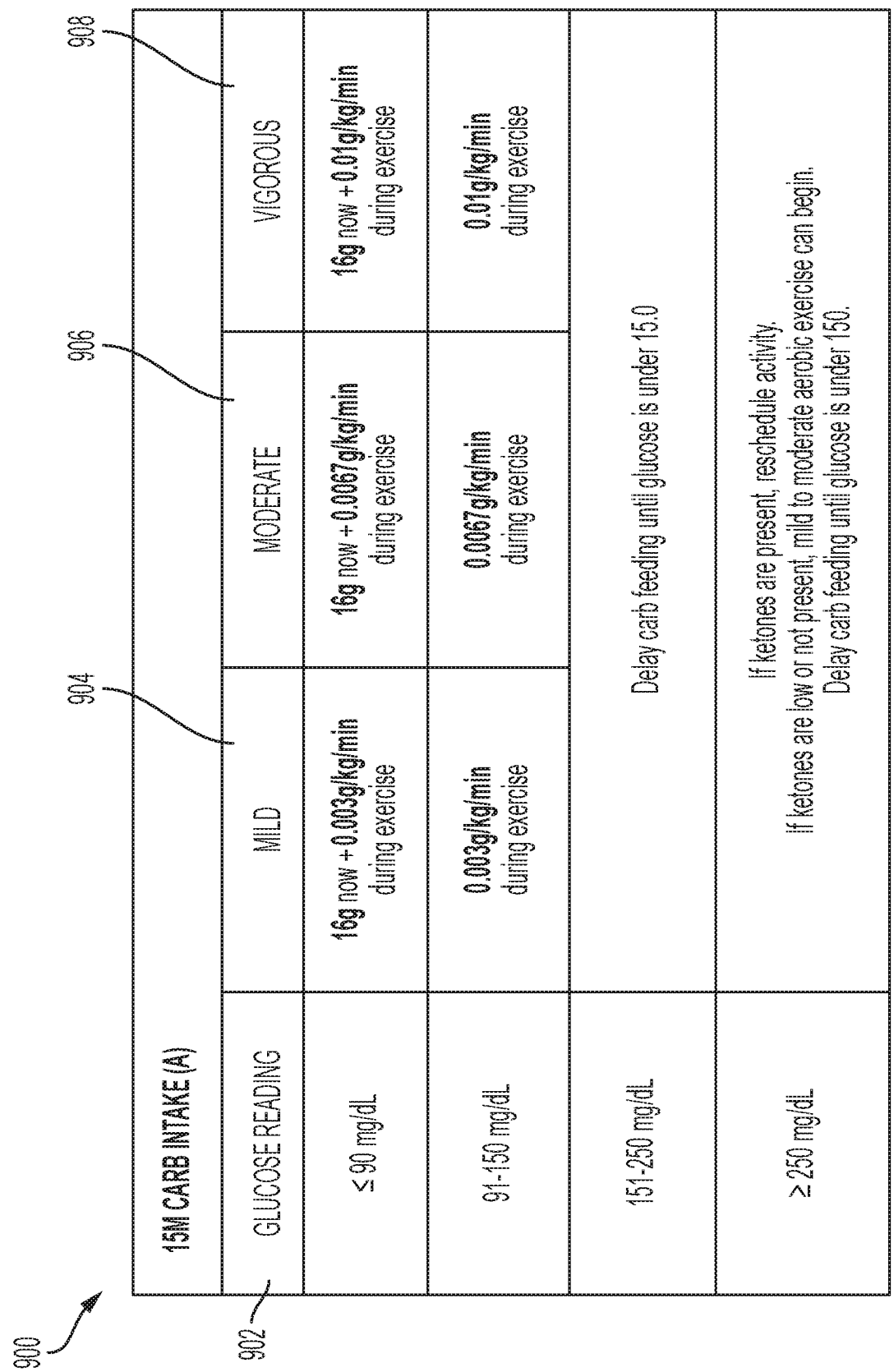

In some embodiments, the computing device is configured to determine and provide an initial recommendation for a mixed aerobic and anaerobic exercise. FIGS. 7A-7B shows an exemplary computerized method 700 for providing an initial recommendation for a mixed aerobic and anaerobic exercise, according to some embodiments. If, for example, the exercise is scheduled within a threshold time period of the exercise (e.g., within one hour), the method 700 starts at step 702 in FIG. 7A. At step 702, the computing device determines whether the user will be taking bolus insulin within three hours before the start of the exercise. If no, the method proceeds to step 704, otherwise the method proceeds to step 706. At step 704, the computing device determines whether the user is wearing an insulin pump. If yes, the method proceeds to step 708 and provides a recommendation for a basal reduction (B), discussed further herein in conjunction with FIG. 7D. If no, the method proceeds to step 710 and provides a recommendation for carb intake.

Turning back to step 706, if the user has not already taken the bolus dose, the method proceeds to step 712 and provides a recommendation for a bolus reduction, as discussed further in conjunction with FIG. 7F. If the user has already taken the bolus dose, the method proceeds to step 714 and determines if the user is wearing an insulin pump. If the user is wearing an insulin pump, the computing device proceeds to step 716 and recommends a basal reduction (A), discussed further in conjunction with FIG. 7C. If the user is not wearing an insulin pump, the method proceeds to step 718 and recommends a carb intake.

If, for example, the exercise is not scheduled within a threshold time period of the exercise (e.g., within one hour), the method 700 starts at step 720 in FIG. 7B. At step 720, the computing device determines whether the user will be taking a bolus insulin within three hours before the start of exercise. If no, the method proceeds to step 722 and determines whether the user is wearing an insulin pump. If no, then the method does not provide an initial recommendation. Otherwise, the method proceeds to step 724 and recommends a basal reduction (D) discussed further in conjunction with FIG. 7E. Turning back to step 720, if yes, the method proceeds to step 726 and determines whether the user already took the bolus dose. If no, the method proceeds to step 728 and determines if the user has a scheduled bolus within 1 hour of the workout. If no, the method proceeds to step 730 and recommends a bolus reduction. If yes, the method proceeds to step 732 and recommends a bolus reduction (e.g., as discussed in FIG. 7F, which shows the recommendation can vary depending on the amount of time to the workout). Referring back to step 726, if the user already took the bolus dose, at step 734 the system determines whether the user is wearing an insulin pump. If no, the computing device provides no initial recommendation. If yes, the computing device proceeds to step 736 and recommends a basal reduction (C), discussed further in conjunction with FIG. 7E.

FIG. 7C shows a table 740 illustrating exemplary logic that can be used to determine an initial recommendation for a basal adjustment (A), which is determined based on the glucose 742 of the user to provide an associated recommendation 744. For example, if the user's glucose is less than or equal to 90 mg/dL, the computing device provides an initial recommendation to consume 16 g of glucose tabs and to reduce basal rate by 50% starting now through the exercise duration. FIG. 7D shows a table 750 illustrating exemplary logic that can be used to determine a basal adjustment (B), which is determined based on the user's glucose 752 to provide an associated recommendation 754. FIG. 7E shows a table 760 illustrating exemplary logic that can be used to determine a basal adjustment (C) and a table 770 illustrating exemplary logic that can be used to determine a basal adjustment (D). FIG. 7F shows a table 780 illustrating exemplary logic that can be used to determine a bolus adjustment, which can be determined based on the exercise intensity 782 and whether the exercise is within 30-60 minutes (784), or more than 60 minutes (786) away.

Turning back to FIG. 4, at step 406, the computing device determines whether it is time for performing an updated analysis for the exercise (e.g., such as determining whether to display any further recommendations). For example, the computing device can be configured to determine whether to provide an additional recommendation at certain time periods before and/or after the exercise, such as one hour before the exercise, fifteen minutes before the exercise, fifteen minutes after the exercise, and/or the like.

The computing device can be configured to provide the additional recommendation based on the time before the exercise and/or the type of exercise. For example, FIG. 8A shows an exemplary table 800 illustrating logic that can be used to determine and provide a recommendation for carb intake one hour before an aerobic exercise, according to some embodiments. The computing device determines the recommendation based on the user's glucose level 802 to provide the corresponding recommendation 804. For example, if the user's glucose is between 91-150 mg/dL, the computing device provides no recommendation (e.g., because the user's glucose is on track for the workout). FIG. 8B shows an exemplary table 810 illustrating logic that can be used to determine and provide a recommendation one hour before the exercise for an anaerobic exercise, according to some embodiments. The computing device determines the recommendation based on the user's glucose level 822 and whether the user is wearing a pump (814) or no pump (816). For example, if the user's glucose is between 151-250 mg/dL and the user is wearing a pump, the computing device recommends that the user temporarily increase the basal rate by 20% until the glucose is 120-150 mg/dL. FIG. 8C shows an exemplary table 820 illustrating logic that can be used to determine and provide a recommendation for carb intake one hour before a mixed aerobic and anaerobic exercise, according to some embodiments. The computing device determines the recommendation based on the user's glucose level 822 to provide the corresponding recommendation 824. For example, if the user's glucose is less than 90 mg/dL, the computing recommends the user take 16 g of carbs now.

In some embodiments, the system can be configured to provide a further check-in and potential new recommendation, such as fifteen minutes before the exercise. As discussed herein, the recommendations can depend on the type of exercise and/or other factors. FIGS. 9A-9D provide examples of a fifteen minute check-in prior to the workout for aerobic exercise, according to some embodiments. Each of FIGS. 9A-9D represent different exemplary logic for performing a fifteen minute check-in prior to the workout for aerobic exercise. In some cases, the system can select one of the logical schemes depicted by one of FIGS. 9A-9D depending on patient or treatment characteristics—such characteristics may include (but is not limited to) whether the user is wearing an insulin pump, whether the user took a reduced bolus dose or decreased his/her basal rate leading up to the exercise, and/or whether the user ingested food or carbs leading up to the exercise. The system can make the selection of which logical scheme to apply based on previous determinations about the patient and/or his/her treatment leading up to the exercise according to the techniques discussed herein. For example, the system can make the selection based on determinations made during steps depicted and described in FIGS. 5A-5B, when providing an initial recommendation to the patient. FIG. 10 provides an example of a fifteen minute check-in prior to the workout for anaerobic exercise, according to some embodiments.

FIGS. 11A-11C provide examples of a fifteen minute check-in prior to the workout for a mixed aerobic and anaerobic exercise, according to some embodiments. Similar to FIGS. 9A-9D, FIGS. 11A-11C represent different exemplary logic for performing a fifteen minute check-in prior to the workout for mixed aerobic and anaerobic exercise. The system can also select one of the logical schemes depicted by one of FIGS. 11A-11C depending on the aforementioned patient or treatment characteristics. For example, the system can make the selection based on determinations about the patient and/or his/her treatment made during steps depicted and described in FIGS. 7A-7B, when providing an initial recommendation to the patient.

Referring to FIGS. 9A-9D, FIG. 9A shows table 900 illustrating exemplary logic that can be used for determining the recommendation based on the user's glucose level 902 as well as whether the exercise is mild (904), moderate (906) or vigorous (908). The logic represented by table 900 can be reached, for example, based on previous determinations according to the techniques discussed herein. For example, the logic can be reached from steps 516, 518 and 510 from FIG. 5A (and therefore the resulting logic that would cause the method 500 to perform these steps in FIG. 5A).

FIG. 9B shows table 910 illustrating exemplary logic that can be used for determining the recommendation based on the user's glucose level 912 as well as whether the exercise is mild (914), moderate (916) or vigorous (918). The logic represented by table 910 can be reached, for example, based on previous determinations according to the techniques discussed herein. For example, the logic can be reached from steps 536 from FIG. 5B.

FIG. 9C shows a table 920 illustrating exemplary logic that can be used for determining the recommendation 924 based on the user's glucose level 922. The logic represented by table 920 can be reached, for example, based on previous determinations according to the techniques discussed herein. For example, the logic can be reached from steps 508, 512, 524, 530, 532, and/or a "no" from step 522 in FIGS. 5A-5B.

FIG. 9D shows table 930 illustrating exemplary logic that can be used for determining the recommendation based on the user's glucose level 932 as well as whether the exercise is mild (934), moderate (936) or vigorous (938). The logic represented by table 930 can be reached, for example, based on previous determinations according to the techniques discussed herein. For example, the logic can be reached from a "no" at step 534 in FIG. 5B.

Referring to FIG. 10 shows table 1000 illustrating exemplary logic that can be used for determining the recommendation based on the user's glucose level 1002 as well as whether the user is wearing a pump (1004) or not wearing a pump (1006).

Referring to FIGS. 11A-11C, FIG. 11A shows a table 1100 illustrating exemplary logic that can be used for determining the recommendation 1104 based on the user's glucose level 1102, FIG. 11B shows a table 1110 illustrating exemplary logic that can be used for determining the recommendation 1114 based on the user's glucose level 1112. FIG. 11C shows a table 1120 illustrating exemplary logic that can be used for determining the recommendation 1124 based on the user's glucose level 1122. The logic represented by tables 1100, 1110 and 1120 can be reached, for example, based on previous determinations according to the techniques discussed herein. For example, table 1100 can be reached from steps 710, 716, or a "no" from step 722 in FIGS. 7A-7B, table 1110 can be reached from steps 718 or a "no" from step 734 in FIGS. 7A-7B, and table 1120 can be reached from steps 708, 712, 724, 730, 732 or 736 in FIGS. 7A-7B.

Figure 12A:
FIG. 12A shows an exemplary table illustrating logic that can be used to provide a recommendation based on the user's glucose level for aerobic exercises, according to some embodiments.

In some embodiments, as described herein the computing device can be configured to provide a further check-in and potential new recommendation after the exercise (e.g., an aerobic cool-down), such as fifteen minutes after the exercise. For example, the computing device can monitor the user (e.g., heart rate) to determine an end of the exercise, request the user indicate an end of the exercise, and/or ask the user to enter an estimated end time of the exercise. FIGS. 12A, 12B and 12C show exemplary tables 1200, 1210 and 1220 that illustrate logic that can be used to provide a recommendation based on the user's glucose level for aerobic, anaerobic, and mixed exercises, respectively.

In some embodiments, this post-exercise check-in and potential recommendation can be provided to users in the form of a push notification. For example, when users have been active during a day (e.g., has completed an exercise session, or an exercise session that satisfies a minimum intensity or duration threshold), the user can be provided with a push notification since the user has been active and may need to make some adjustments. In some cases, this push notification may provide recommendations to the user for avoiding hypoglycaemia when sleeping after an exercise session. This push notification may appear as a message or dialog box on the users smartphone screen, and may be provided to the user at a specified time interval after an exercise session (e.g., immediately after an exercise session, or 15 minutes, 30 minutes, or 1 hour after an exercise session), or at a specified time of day (e.g., at 9 pm, at which time the user is expected to be preparing for sleep). In some embodiments, the push notification can provide tailored recommendations to the user, such as how much carbs to take, dosing recommendations (e.g., to cut insulin), and/or the like. As another example, the push notification may notify the user that the user's insulin sensitivity may be increased after an exercise session, and as a result the user may need less insulin compared to other days where the user did not exercise. As another example, if the user is wearing a CGM, the push notification may recommend adjust to the CGM alarms to increase its sensitivity to ensure an alarm is triggered in case of post-exercise or nocturnal hypoglycemia. This can be done, for example, by recommending that the user increase the glucose level threshold at which a CGM would alert the user to a potential hypoglycemic episode. As another example, if the user is using finger sticks, the push notification may recommend that the user set an alarm to take a blood glucose measurement in the middle of the night after an exercise session. As yet another example, the push notification may recommend that the user consume protein and/or fat before bedtime (e.g., drinking a cup of milk before bed) to mitigate or decrease the likelihood of hypoglycemic episodes while the user is asleep.

In some embodiments, the user can be presented with visual displays guiding the user through the check-in process. In some embodiments, the user can be presented with a visual timeline that includes a visual indicator indicating each of one or more times at which the user will be prompted to provide input data (e.g., of a scheduled glucose measurement) and a separate visual indicator indicating the future exercise start time. For example, the timeline can include a visual indicator indicating a time at which the user will be prompted to provide a first scheduled glucose value (e.g., one hour from the exercise), a visual indicator indicating a second time at which the user will be prompted to provide another scheduled glucose value (e.g., fifteen minutes from the exercise), a visual indicator indicating the exercise start time, and a visual indicator indicating a time at which the user will be prompted to provide a post-exercise glucose value (e.g., fifteen minutes after the exercise).

Referring further to FIGS. 3A-3I, FIG. 3F includes a display 350 that shows the computing device's initial recommendation. In this example, the patient's glucose is on target so the patient does not need to take any action. If the patient's glucose had been high or low, for example, the computing device may recommend adjusting the patient's bolus or basal rate as discussed herein. The display 350 includes a "View Timeline" button 352 that, when selected, takes the user to display 360 in FIG. 3G, which as described herein can show a timeline 362 of the check-in events leading up to the exercise session, the session itself (as indicated by the bolded portion on the timeline curve), and check-in events after the session. The user can see all the events that will take place throughout the day leading up to the scheduled exercise. In this example, since the exercise session is only approximately half an hour away (the time on the mobile phone is 1:32 pm, and the exercise is scheduled for 2 PM), there is only one check-in 364 which is fifteen minutes before exercise start shown as 366. If the exercise session had been further away, such as more than 1 hour away, there would have been additional check-ins, such as another check-in shown on the timeline 1 hour before exercise start (e.g., as discussed with respect to FIG. 13A). The user can touch each symbol on the timeline to display more detail along the bottom of the display. For example, touching check-in 364 indicates that it is a glucose check-in at 1:45 pm that must be performed before starting the activity.

Figure 3H:
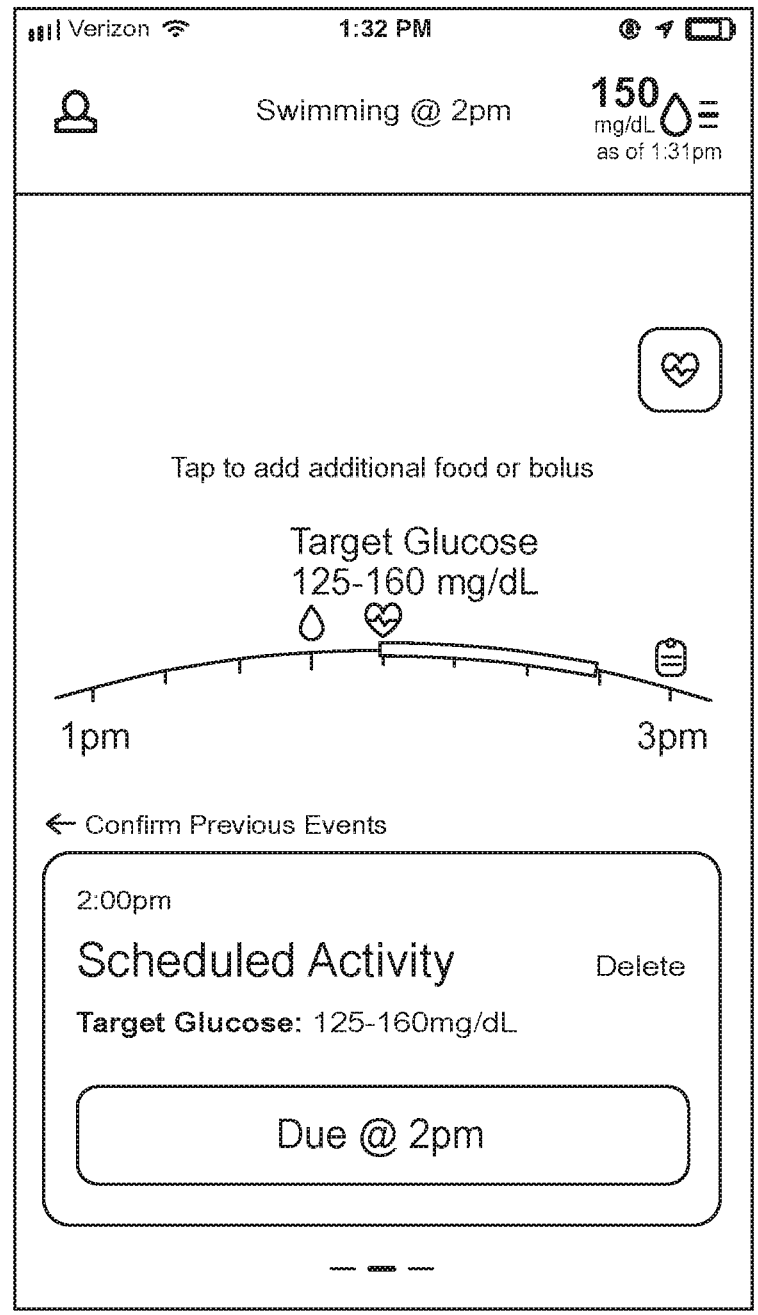
Figure 3I:
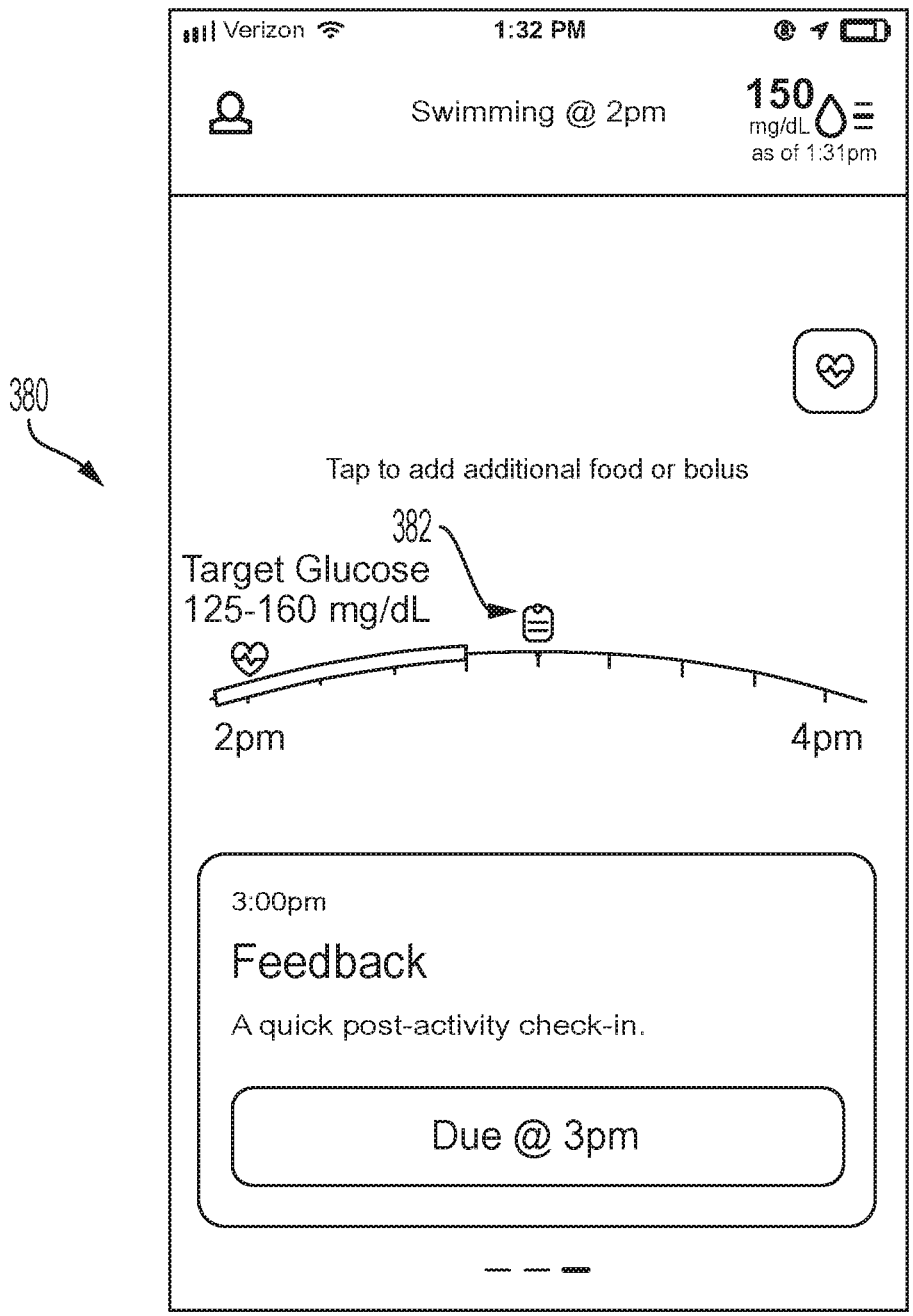

FIG. 3H shows display 370 illustrating how the display 360 changes when the user touches the exercise session symbol 366, which shows the scheduled activity starting at 2 pm and ending at 2:45 pm (again, as illustrated by the bolded portion of the timeline curve) and that the user has a target glucose value of 125-160 mg/dL for the exercise. FIG. 3I shows display 380 showing how the display updates when the user selects the post-exercise check-in icon 382, which causes the display to show a post-activity feedback is due at 3 pm.

Figure 13A:
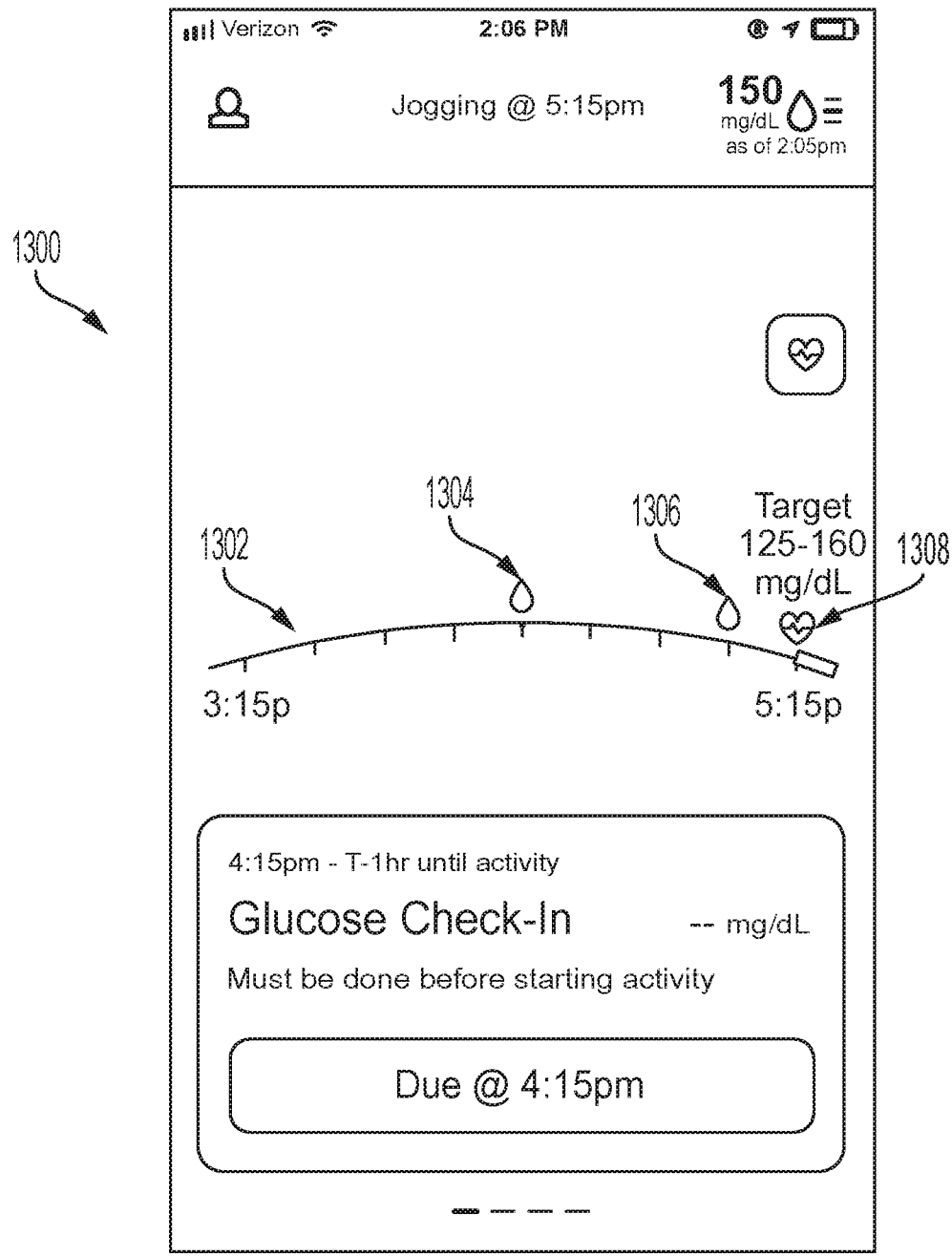
FIGS. 13A-13D show another exemplary series of displays for planning a jogging exercise that is more than one hour away, according to some embodiments.
Figure 13B:
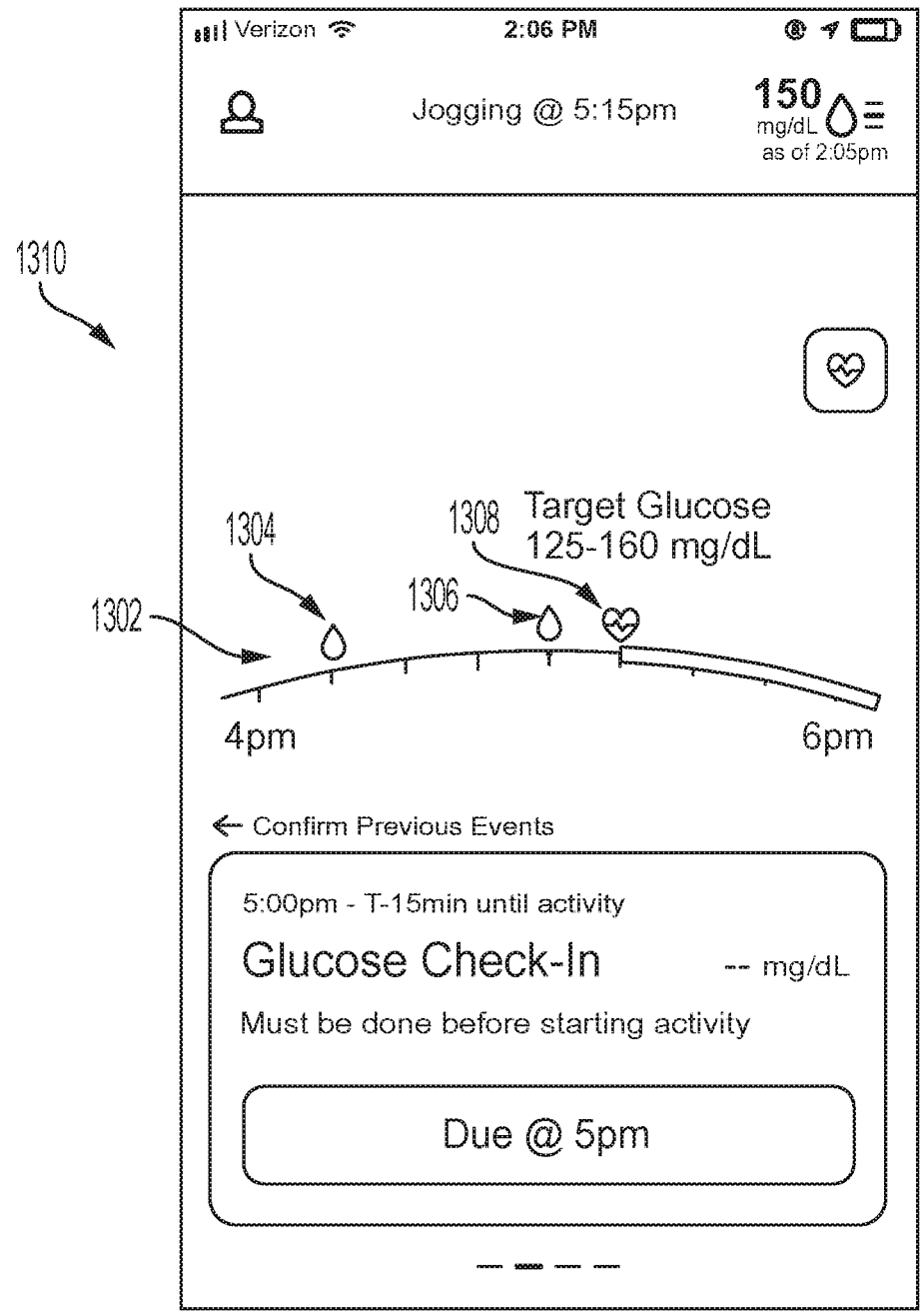
Figure 13C:
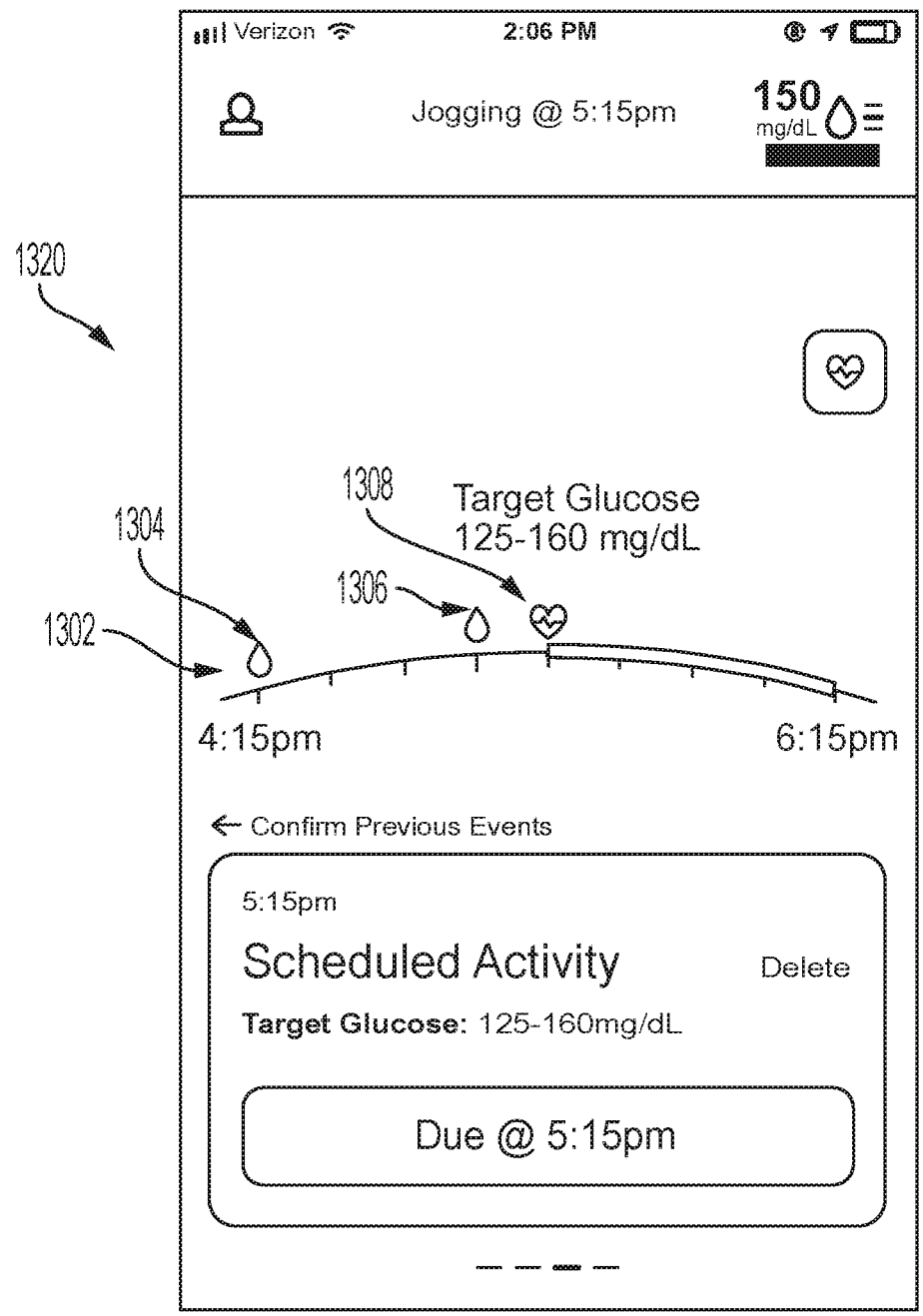
Figure 13D:
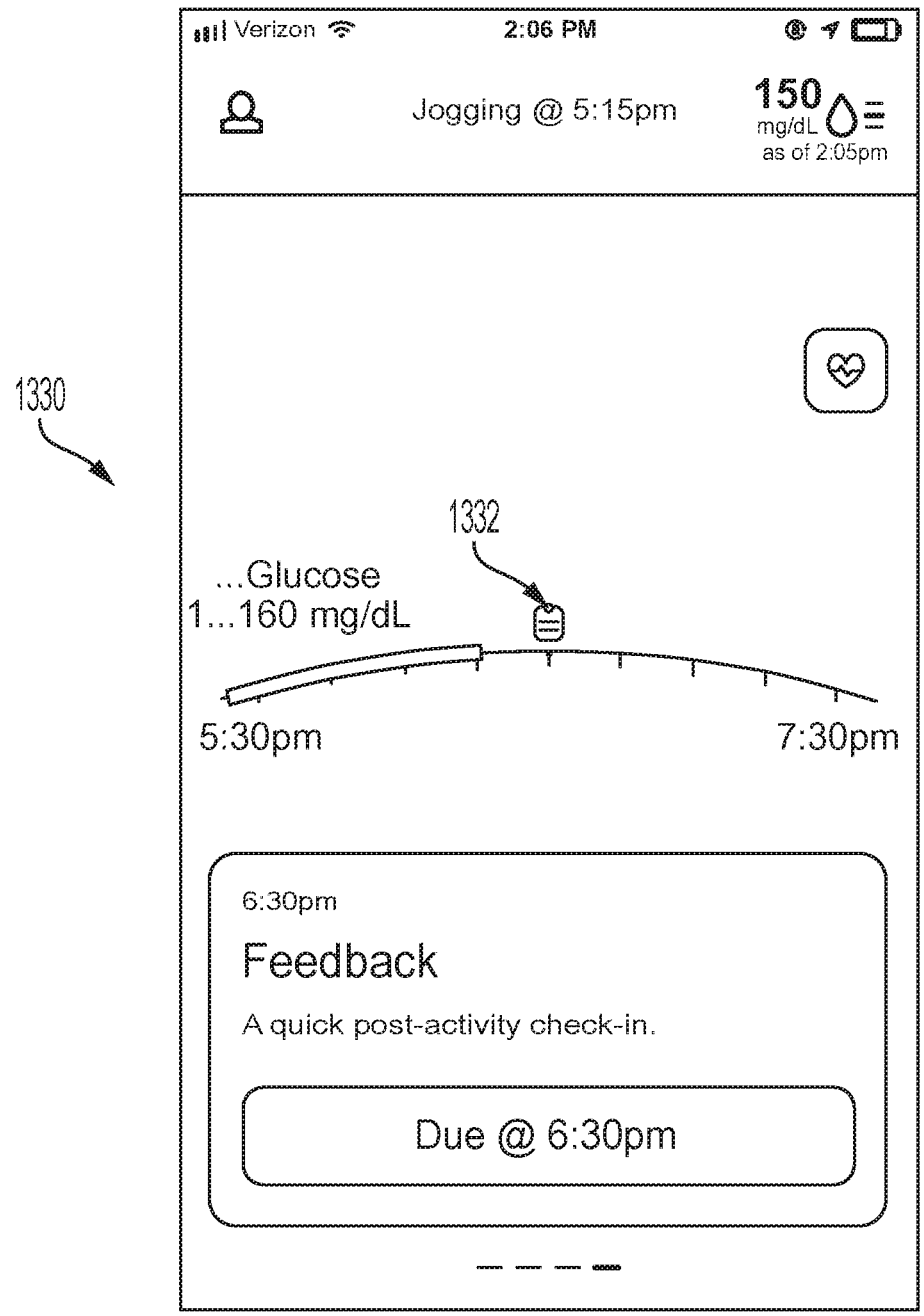

FIGS. 13A-13D show another exemplary series of displays for planning a jogging exercise that is more than one hour away, according to some embodiments. FIG. 13A shows display 1300 with a timeline 1302, which includes a one hour check-in icon 1304, a fifteen minute check-in icon 1306, and an exercise icon 1308. The one hour check-in icon 1304 is selected in display 1300, and the display therefore summarizes at the bottom of the screen that a glucose check-in is required one hour out from the exercise. FIG. 13B shows display 1310 when the fifteen minute check-in icon 1306 is selected, and the text is updated to show that a glucose check-in is required fifteen minutes out from the exercise. FIG. 13C shows display 1320 when the exercise icon 1308 is selected for the scheduled activity. FIG. 13D shows display 1330 when the post-exercise icon 1332 is selected, which updates the display to indicate a post workout check-in is due at that time.

Figure 14:
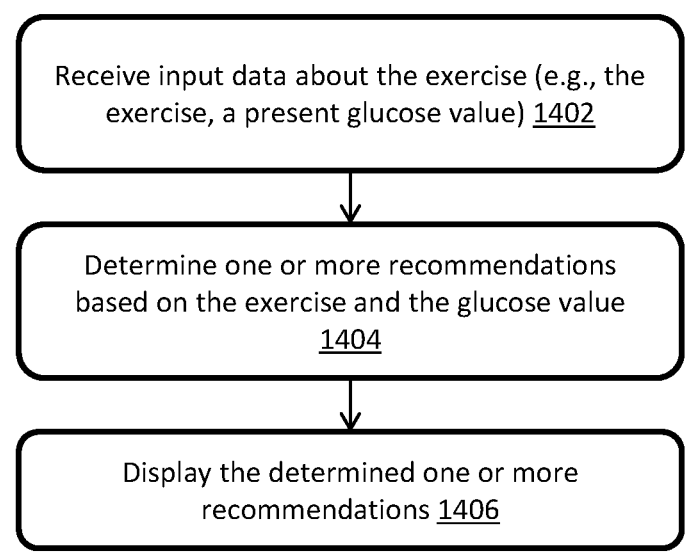
FIG. 14 shows an exemplary computerized method for monitoring the user during an exercise, according to some embodiments.

In some embodiments, the techniques described herein provide for monitoring the patient during an exercise, such as to keep track of medical and/or physiological data for customization, to provide further recommendations to the user, and/or the like. FIG. 14 shows an exemplary computerized method 1400 for monitoring the user during an exercise, according to some embodiments. At step 1402 the computing device receives input data about the exercise. At step 1404, the computing device determines one or more recommendations based on the input data. At step 1406, the computing device displays, via a display of the computing device, the one or more recommendations.

Referring to step 1402, the input data can include data indicative of the exercise being conducted by the patient, one or more present glucose value(s) of the patient while conducting the exercise, heart rate data, and/or other information about the patient and/or the exercise. As explained herein, the data can be manually input by the patient, received from another device (e.g., transmitted from a CGM, or from a wearable sensor), and/or the like.

Referring step 1404, the computing device determines one or more recommendations based on the input data. These recommendations are displayed to the user in step 1406. In some embodiments, the computing device can recognize when the user's glucose levels stray outside of an ideal glucose range or derive trends in the user's glucose values during the exercise, and can determine one or more recommendations accordingly. The techniques can be configured to maintain the user's glucose levels within a target range throughout the activity. For example, if the user is conducting an aerobic exercise and the user's glucose levels decrease below a certain minimum threshold, or are observed to trend downward such that the patient may experience hypoglycemia in the near future, then the computing device can recommend that the user ingest carbohydrates, administer glucagon, or perform an anaerobic activity to increase the user's glucose levels. As another example, if the user is conducting an anaerobic exercise and the user's glucose levels increase above a certain maximum threshold, or are observed to trend upward such that the patient may experience hyperglycemia in the near future, then the computing device can suggest that the user administer insulin, or perform a new aerobic activity to reduce the user's glucose levels. As a further example, if the user is conducting a mixed activity and the user's glucose levels start to rise or fall, then the computing device can make an appropriate new recommendation accordingly.

In some embodiments, the techniques can use heart rate data to monitor the intensity of the exercise for the user. The techniques can be configured to take into account both the user's heart rate and glucose levels to determine a recommendation. For example, the computing device can correlate the user's heart rate level to the user's glucose level, such as determining how reaching a certain heart rate level can cause a drop in the user's glucose. As another example, the computing device can determine the amount of time between onset of the user's peak heart rate and a glucose drop.

The user's heart rate can be correlated to the nature of the activity (e.g., aerobic and/or anaerobic activity), which can be used to draw inferences regarding the user's glucose levels. For example, when a person sprints, their heart rate can increase quickly, and their glucose levels can also increase. In contrast, when a user slows down the pace of an activity, their heart rate should similarly decrease, and their glucose levels can also decrease. The techniques can use heart rate to monitor and/or make recommendations based on the user's performance of the activity (e.g., to use a mix of jogging and sprinting to maintain glucose levels). For example, if the system detects that at a heart rate of 120 beats per minute the user's glucose is dropping, the computing device can recommend that the user speeds up to a faster pace to increase the user's heart rate, thereby engaging in anaerobic activity to increase the user's glucose levels. As another example, the system could recommend the user conduct weight training exercises to raise the user's heart rate, and thereby increase the user's glucose levels. Therefore, heart rate information can be used to determine the type of activity (e.g., aerobic and/or anaerobic) to provide custom recommendations to a user.

In some embodiments, thresholds can be adjusted for during-exercise recommendations based on the user. For example, there may be user-specific issues for exercises, such as hypoglycemic unawareness (e.g., where a user doesn't exhibit the typical symptoms leading up to hypoglycaemia, such as sweating, turning pale, etc.). Therefore, the thresholds used to trigger recommendations for an exercise can be modified on a per-user basis. For example, for a user with hypoglycemic unawareness, the techniques can be designed to take into account potentially higher minimum glycemic thresholds and/or shorter detection time windows to detect hypoglycemic indications. Modifying the computing device to provide custom recommendations to a user is discussed further below in conjunction with FIG. 16.

Figure 15:
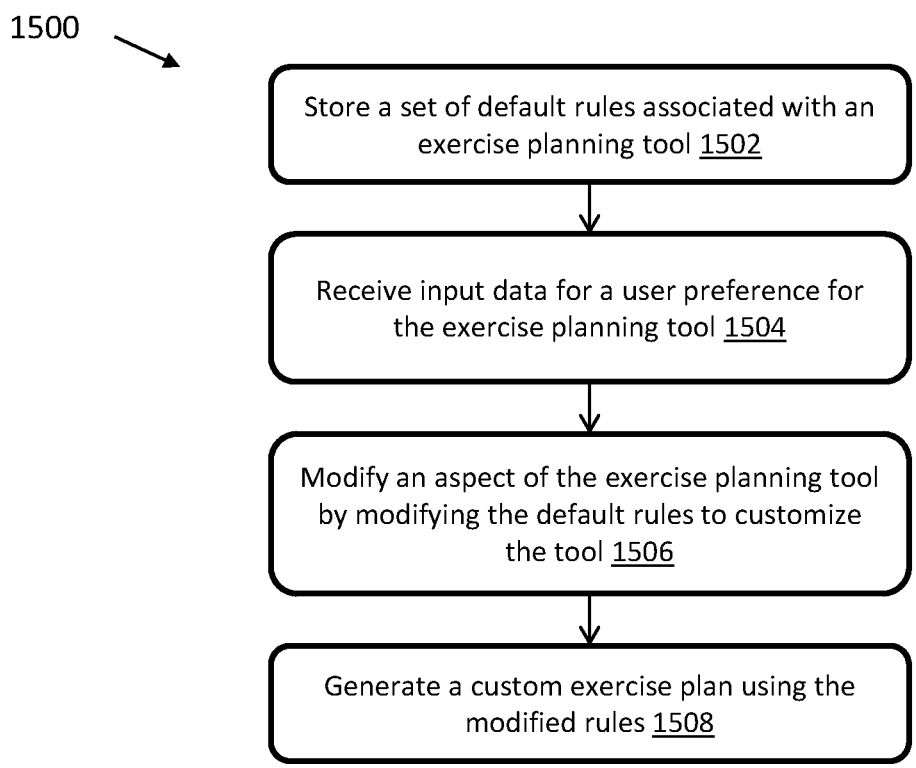
FIG. 15 shows an exemplary computerized method for customizing exercise planning for a patient with diabetes, according to some embodiments.

In some embodiments, the techniques are configured to customize the exercise planning features discussed herein based on user preferences, such as user goals for exercise (e.g., to lose weight, build muscle, and/or the like). FIG. 15 shows an exemplary computerized method 1500 for customizing exercise planning for a patient with diabetes, according to some embodiments. At step 1502, the computing device stores a set of default rules associated with an exercise planning tool. At step 1504, the computing device receives input data indicative of a user preference for the exercise planning tool.

At step 1506, the computing device modifies an aspect of the exercise planning tool by modifying the set of default rules to customize the exercise planning tool for the patient based on the input data. At step 1508, the computing device generates an exercise plan for the patient based on the modified aspect of the exercise planning tool. By customizing the exercise planning tool, the exercise plan can be different than what would otherwise be generated using the unmodified set of default rules so that it is customized to the user's preferences.

Referring to step 1502, the default rules can include one or more rules and/or associated configuration data used to implement one or more aspects of the techniques described herein, such as for developing an exercise plan for a patient with diabetes.

Referring to step 1504, the user preferences may include the user's goals for engaging in exercise. Examples of goals can include losing body weight, maintaining the user's body weight, building muscle, maintaining muscle, training for a certain event (e.g., a half marathon, marathon, etc.), performing an exercise (e.g., an exercise the user needs to work up to in order to perform safely), improving flexibility, maintaining flexibility, and/or the like. The user preferences may also include indications from the user that certain types of exercise are preferred over other types of exercise. For example, the user may provide input that indicates aerobic exercise is preferred over anaerobic exercise (or vice versa), or that a certain type of exercise is preferred over another type of exercise in the same category (e.g., the aerobic exercise of walking is preferred over the aerobic exercise of working out on an elliptical).

Referring to step 1506, the computing device can monitor the exercise planning tool by modifying, for example, one or more aspects of the tool used to plan and/or monitor the exercise. For example, the computing device can monitor one or more rules or configuration data (e.g., used by the rules and/or other aspects of the planning tool, and/or the like). The modification can modify recommendations provided to the user, as explained in conjunction with step 1508.

Referring to step 1508, the custom exercise plan can include a customized recommendation that is different than a default recommendation, such as the recommendations discussed herein that can be provided before an exercise, during an exercise, and/or after an exercise. The computing device can use input data to plan the custom exercise plan as discussed herein, such as the exercise type, exercise time, glucose level, heart rate, and/or the like. In some embodiments, the user's desired customizations can be used to control the overall decision-making of the algorithms of the techniques discussed herein. For example, if the user is hoping to use exercise to lose weight, then the computing device can modify the tool so that it does not recommend activities that could reduce the user's ability to lose weight. For example, rather than recommend carb feeding in order to prevent hypoglycemia, instead the application may suggest other recommendations to prevent hypoglycemia, such as performing an anaerobic exercise, a mixed activity exercise, reducing a bolus insulin dose before or during exercise by even more than the application would have recommended otherwise, reducing the user's basal rate before or during exercise by even more than the application would have recommended otherwise, and/or the like. As another example, the system may be configured to sort an original order of a set of recommended exercises to provide a set of preferred exercises before other less-preferred exercises based on the user's preferences (e.g., whereas the computing device may otherwise provide the original order of recommended exercises). The preferred exercises may be identified based on the user's previously-expressed preferences (e.g., if the user indicates he/she prefers running to weight-lifting), based on the user's expressed goals (e.g., if the user indicates he/she is trying to lose weight, running or jogging may be identified as a preferred exercise), based on user feedback to previous exercise sessions (e.g., if the user indicates he/she had a good exercise session while swimming, swimming may be identified as a preferred exercise), or based on the user's glucose levels during previous exercise sessions (e.g., if the user's glucose levels are observed to remain within an ideal range more consistently while running than while weight-lifting, running may be identified as a preferred exercise; alternatively, if the user's glucose levels are observed to remain within the ideal range during one or more swimming sessions, swimming may be identified as a preferred exercise).

In some embodiments, the techniques can include customizing the exercise planning features based on user-specific information, such as based on user-specific treatment aspects, physiological aspects, and/or the like. For example, the techniques can include a predetermined general set of recommendations and/or guidelines (e.g., such as "reduce basal rate by 80%" or "cut bolus dose by 50%") designed as a one-size-fits-all initial set of recommendations designed to apply broadly to most users. Over time, the computing device can adapt the techniques to the user, such as based on the user's historical glucose response to such interventions. If, for example, the user went hyperglycemic the last time the user cut the insulin basal rate or bolus dose by 80% before engaging in exercise, the computing device may instead recommend cutting the basal rate or bolus dose of insulin by less at the next exercise session (e.g., by 70%).

Conversely, if the user went hypoglycemic the last time the user cut the insulin basal rate or bolus dose by 80% before engaging in exercise, the computing device may instead recommend cutting the basal rate or bolus dose of insulin by more at the next exercise session (e.g., by 90%). By maintaining a log of the user's historical glucose response to interventions, the computing device can customize the general set of recommendations and/or guidelines to the user's specific glucose responses to past interventions. Therefore, in some embodiments, the techniques can be designed to make it easy for a user to choose an activity with a high likelihood of user enjoyment in addition to having a high likelihood of safe glucose levels.

Figure 16:
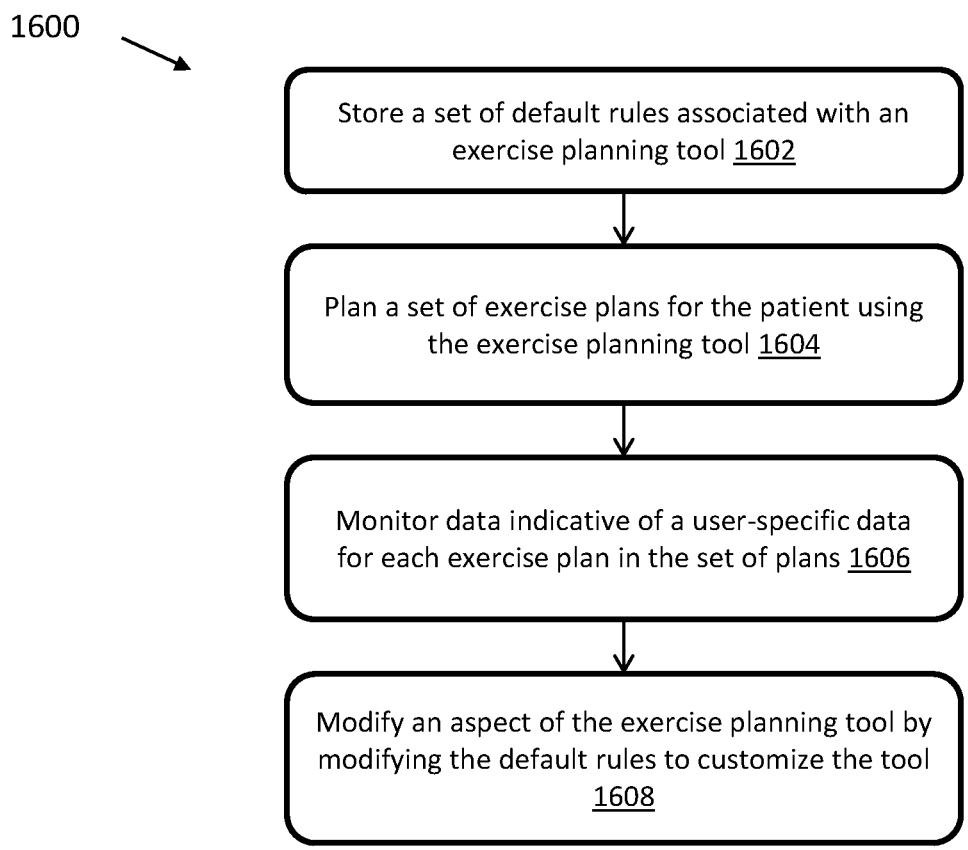
FIG. 16 shows an exemplary computerized method for customizing an exercise planning tool based on user-specific information, according to some embodiments.

FIG. 16 shows an exemplary computerized method 1600 for customizing an exercise planning tool based on user-specific information, according to some embodiments. At step 1602, the computing device stores a set of default rules associated with an exercise planning tool for developing an exercise plan. At step 1604, the computing device plans a set of exercise plans for the user. At step 1606, for each exercise plan, the computing device monitors data indicative of user-specific data. At step 1608, the computing device modifies an aspect of the exercise planning tool by modifying the set of default rules to customize the exercise planning tool for the patient based on the monitored data.

Referring to steps 1604-1606, the user-specific data monitored for each exercise plan can include a treatment aspect of the patient, a physiological aspect of the patient, and/or other user-specific data. The treatment aspects can include monitoring one or more aspects related to the user's diabetic treatment, such as monitoring bolus insulin doses, basal rates, and/or the like. The physiological aspects can include monitoring a set of heartrate measurements, a set of glucose measurements, a set of food ingestions, perspiration, user temperature (e.g., of the user's skin), environmental temperature (e.g., of the location for the exercise), user hydration (e.g., as reported by user, or based on user's heart-rate), user brain or heart activity (e.g., such as by electroencephalogram (EEG) or Electrocardiogram (EKG)), user activity or movement (e.g., as measured by an accelerometer or gyroscope worn on the user's body), how well the user slept the previous night(s), cortisol levels, ketone levels, and/or the like. In some embodiments, the techniques can monitor the user's starting glucose level (e.g., upon starting the exercise), the duration of the exercise, the intensity of exercise (e.g., based on heart rate information, category of exercise, time of exercise, and/or the like), the user's glucose levels during the exercise, the user's ending glucose level upon completion of the exercise, user feedback after the exercise (e.g., understanding how the user feels after the exercise, such as "good," "bad," and/or a numerical rating indicating the user's satisfaction with the exercise and/or his or her glucose levels during or after the exercise etc.), and/or the like. In some embodiments, the techniques can monitor health factors of the user, such as whether the user is taking medications, the user's menstrual cycle phase, whether the user is taking steroids (e.g., for asthma, other health reasons), whether the user is sick, whether the user stressed, whether the user suffers from any physical injuries, and/or other health factors.

Referring to step 1608, as discussed in conjunction with FIG. 15, the computing device can modify the rules in various ways, such as by modifying the rules, modifying configuration data, and/or the like. Thus, when the next exercise is planned, the exercise plan is customized to the patient based on the modification(s) performed at step 1608. As discussed herein, the exercise plan can include various recommendations, such as recommendations to adjust a bolus dose, a basal rate, an amount of carbohydrates to ingest, recommending exercises, and/or the like as discussed herein.

In some embodiments, recommendations can be customized based on information obtained at various phases leading up to, during, and/or after an exercise. For example, the user can be monitored and/or provided with recommendations during a time period leading up to commencement of the exercise (e.g., the hour leading up to the exercise). This period can be monitored to customize recommendations to the user regarding how to manage his or her insulin and/or carbohydrate intake leading up to the exercise to ensure he or she begins the exercise with glucose levels within a target ideal range. The user can also be monitored and/or provided with recommendations during a first phase of the exercise (e.g., the first ten minutes, the first thirty minutes, etc.). The first phase can be monitored and/or used to provide recommendations to a user since during some exercises, for example, a user's glucose levels may drop quickly during that period. The user can also be monitored during a second phase of the exercise (e.g., after the first ten minutes, or first thirty minutes, until the conclusion of the exercise). The user's glucose levels may exhibit different behaviour during this second phase of the exercise, and so the second phase of the exercise may be monitored and/or analysed using a separate set of rules or processes to provide recommendations. As another example, the user can be monitored and/or provided with recommendations for an initial post-exercise period, such as for the first thirty minutes after the exercise, forty minutes after the exercise, etc. For example, the post-exercise phase can be monitored since a user's glucose levels could increase quickly during that period. As a further example, a user can be monitored and/or provided with recommendations for a longer post-exercise period, such as for eight to twelve hours, or twenty-four hours after an exercise. For example, during such a longer post-exercise period, users may be more insulin-sensitive, so users may need to take less insulin (e.g., recommendations can be provided for a basal adjustment or to ingest carbs). For post exercise periods, for example, a recommendation can be provided for the user to cut their next bolus dose by a percentage, to cut their next basal amount by a percentage, to cut a post-dinner dose by a percentage, and/or the like.

In some embodiments, data of exercises, associated recommendations, and/or other usage data as described herein can be collected from users as they interact with the application to further develop the techniques described herein. For example, the recommendations described herein (e.g., pre-exercise recommendations, recommendations presented during an exercise, recommendations presented after an exercise, etc.) can be based on an initial set of rules established as a starting baseline for the techniques described herein. This initial set of rules can be determined based on baseline recommendations that are expected to apply to the average user in a population of expected users—however, these initial rules may be customized to better fit a specific user by analysing the data described above. Data from each of the periods discussed above (e.g., period leading up to exercise, first phase of exercise, second phase of exercise, initial post-exercise period, and longer post-exercise period) may be analysed across multiple exercise sessions to better customize future recommendations to a specific user. For example, user data can be compiled for recommendations made leading up to the exercise (e.g., basal recommendations, bolus recommendations, glucose checks, carb intake, etc.). The system can build a database and/or set of reports of user interactions, including activity data, glucose measurements, heartrate, etc., as well as responses when people conduct exercises (e.g., regarding whether the user performed the exercise without issue, had issues, etc.). The information can be analysed and used to make the techniques more robust in view of real-world exercise data.

Various ways of modifying an aspect of the exercise planning tool to customize the tool for a particular user are possible. Several non-limiting examples of how this customization may occur are described below.

In some embodiments, the system may be configured to sort an original order of a set of recommended exercises to provide a set of preferred exercises before other less-preferred exercises based on monitored user treatment or physiological data. For example, if the system observes that the user's glucose levels remain within an ideal range more consistently when conducting certain types of exercise (possibly with minimal or no treatment interventions during exercises, i.e., without requiring any administration of insulin or glucagon), the system may be configured to identify those exercises as preferred exercises, and sort the set of recommended exercises to prioritise those preferred exercises. Alternatively, if the system observes that the user has had good glycemic performance (i.e., the user's glucose levels remained within the ideal range) while performing a certain type of exercise, that exercise may be identified as a preferred exercise. As yet another alternative, if the system observes that the user had poor glycemic performance while performing a certain type of exercise, that exercise may be identified as a non-preferred exercise.

In some embodiments, the computing device may be configured to classify and/or further classify exercises for the patient. For example, the computing device can store an original set of classifications of exercises (e.g., aerobic, anaerobic, and/or mixed). The computing device can generate a new set of classifications of the exercises, such as sub-classifications and or different classifications of the exercises. For instance, the computing device may be configured to classify running as an aerobic exercise by default. After several exercise sessions however, the computing device may observe that the user's heart-rate consistently increased above a certain maximum threshold for aerobic exercise, and/or the user's glucose levels increased rather than decreased while running. Based on this experience, the computing device may re-classify running as an anaerobic exercise to customize the exercise tool for a particular user's preference or fitness level. As another example, the computing device may be configured to subdivide the default set of classifications into finer sub-classifications. For instance, the exercise tool may observe that although swimming and jogging are both classified as aerobic exercises by default, the user's glucose levels tend to decrease by a greater amount while swimming than while jogging. As a result, the exercise tool may classify swimming in a separate sub-classification than jogging—although both exercise types remain classified as aerobic exercises, the exercise tool may thereafter recognize and take into account the fact that swimming will likely lead to a greater decrease in glucose levels than jogging. In response to this, the exercise tool may recommend greater decreases in insulin dosages when preparing for swimming rather than jogging. Similar re-classifications, or finer subdivisions of other default exercise categories are also possible.

In some embodiments, the computing device may modify bolus/basal rate recommendations, and/or carb ingestion recommendations, based on monitored data indicative of a user's treatment aspect or physiological aspect in previous exercise sessions. For example, the exercise tool may be configured to recommend cutting an insulin basal rate or bolus dose by 50% under certain circumstances (e.g., given a certain planned exercise session, under a certain starting glucose level). If, however, the tool observes that the last time the user cut basal rate or bolus dose by 50% under those circumstances, the user went hypoglycemic, the tool may instead recommend cutting the basal rate or bolus dose by more (e.g., by 80% or 90%) under similar circumstances in the future. The tool may also recommend ingesting carbs (or ingesting more or less carbs than the default recommendation) in similar circumstances in the future. Similarly, if the tool observed that the user went hyperglycemic, the tool may instead recommend cutting the basal rate or bolus dose by less (e.g., by 20%) under similar circumstances in the future.

In some embodiments, the computing device may customize its recommendations based on the user's monitored heart-rate data during previous exercise sessions. For example, the computing device may observe, over the course of one or more exercise sessions, that the user's glucose levels increase when the user's heart-rate exceeds a certain level (e.g., for anaerobic exercise), or that the user's glucose levels decrease when the user's heart-rate is within a certain range (e.g., for aerobic exercise). Based on these observed heart-rate levels and/or ranges, the computing device may be configured to predict the user's glucose response to certain exercises based on the user's heart-rate. And based on these predictions, the computing device may be configured to recommend at least one of administration of a bolus dose of insulin, ingestion of an amount of carbohydrates, and/or a modified exercise based on this predicted glucose response, before any actual glucose response is observed from a glucose sensor (e.g., a CGM). This can improve the response time of the computing device to potential swings in glucose levels due to exercise.

In yet other embodiments, the computing device may customize its post-exercise check-ins or push notifications based on the user's treatment or physiological data after exercise. For example, the computing device may be configured to instruct the patient to reduce basal or bolus doses of insulin by a certain amount (e.g., 50%) after exercise. This amount may be based on a default guideline generally applicable to the average user in a population of expected users. However, the computing device may observe after one or more exercise sessions that the user would benefit from a greater or lesser decrease in insulin after exercise, based on observations of the user's glucose levels in the hours after an exercise session. The computing device may therefore be configured to tailor post-exercise recommendations based on the user's observed treatment or physiological aspects.

Figure 17:
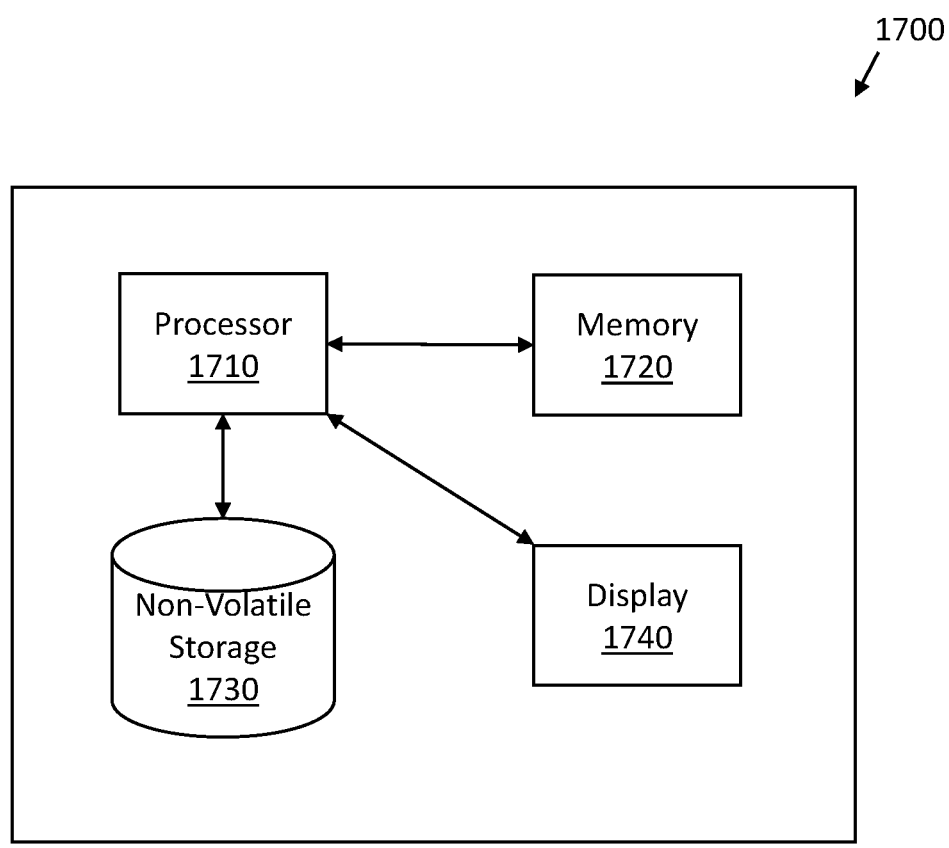
FIG. 17 shows an illustrative implementation of a computer system that may be used to perform any of the aspects of the embodiments.

An illustrative implementation of a computer system 1700 that may be used to perform any of the aspects of the techniques and embodiments disclosed herein is shown in FIG. 17. The computer system 1700 may include one or more processors 1710 and one or more non-transitory computer-readable storage media (e.g., memory 1720 and one or more non-volatile storage media 1730) and a display 1740. The processor 1710 may control writing data to and reading data from the memory 1720 and the non-volatile storage device 1730 in any suitable manner, as the aspects of the invention described herein are not limited in this respect. To perform functionality and/or techniques described herein, the processor 1710 may execute one or more instructions stored in one or more computer-readable storage media (e.g., the memory 1720, storage media, etc.), which may serve as non-transitory computer-readable storage media storing instructions for execution by the processor 1710.

In connection with techniques described herein, code used to, for example, provide tools for diabetic patients to plan exercises may be stored on one or more computer-readable storage media of computer system 1700. Processor 1710 may execute any such code to provide any techniques for planning an exercise as described herein. Any other software, programs or instructions described herein may also be stored and executed by computer system 1700. It will be appreciated that computer code may be applied to any aspects of methods and techniques described herein. For example, computer code may be applied to interact with an operating system to plan exercises for diabetic users through conventional operating system processes.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above. The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. Data structures may have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

Various aspects are described in this disclosure, which include, but are not limited to, the following aspects:

1. A method for recommending one or more types of exercise to a patient with diabetes using a computing device, the method comprising: receiving, by the computing device, input data indicative of (i) a future exercise start time at which the patient intends to begin exercising and (ii) a present glucose value of the patient; determining, by the computing device, an amount of time between a present time and the future exercise start time; determining, by the computing device, one or more recommended exercise types based on the present glucose value of the patient and the amount of time; and displaying, via a display of the computing device, the one or more recommended exercise types.

2. The method of aspect 1, wherein displaying the one or more recommended exercise types comprises: when the amount of time is less than a minimum duration threshold, determining whether the present glucose value is less than a first glucose threshold; displaying a first plurality of exercise types from a first category of exercises if the present glucose value is less than the first glucose threshold; and displaying a second plurality of exercise types from a second category if the present glucose value is greater than or equal to the first glucose threshold, wherein the first plurality of exercise types is different from the second plurality of exercise types.

3. The method of aspect 2, further comprising displaying via the display, when the amount of time is less than the minimum duration threshold, a third plurality of exercise types from a third category of exercises if the present glucose value is between a second glucose threshold and a third glucose threshold.

4. The method of any of aspects 2-3, further comprising displaying via the display both the first plurality of exercise types from the first category of exercises and the second plurality of exercise types from the second category of exercises when the amount of time is greater than or equal to the minimum duration threshold.

5. The method of aspect 3, further comprising displaying via the display the first plurality of exercise types from the first category of exercises, the second plurality of exercise types from the second category of exercises, and the third plurality of exercise types from the third category of exercises when the amount of time is greater than or equal to the minimum duration threshold.

6. The method of any of aspects 2-5, wherein the minimum duration threshold is one hour.

7. The method of any of aspects 2-6, wherein the first category of exercises comprises anaerobic exercises and the second category of exercises comprises aerobic exercises.

8. The method of any of aspects 3-7, wherein the third category of exercises comprises mixed aerobic and anaerobic exercises.

9. The method of any of aspects 2-8, wherein the first glucose threshold is between 130 mg/dL and 160 mg/dL.

10. The method of any of aspects 2-9, wherein the first glucose threshold is between 140 mg/dL and 150 mg/dL.

11. The method of any of aspects 3-10, wherein the second glucose threshold is between 80 mg/dL and 120 mg/dL, and the third glucose threshold is between 140 and 180 mg/dL.

12. The method of any of aspects 3-11, wherein the second glucose threshold is between 95 mg/dL and 105 mg/dL, and the third glucose threshold is between 155 mg/dL and 165 mg/dL.

13. The method of aspects 1-12, wherein the computing device receives the present glucose value of the patient from at least one of a connected glucose meter and manual user input.

14. The method of any of aspects 1-13, further comprising receiving second input data indicative of an Insulin on Board (IOB) amount for the patient, and wherein the one or more recommended exercise types is determined based at least in part on the second input data.

15. A non-transitory computer-readable media comprising instructions that, when executed by one or more processors on a computing device, are operable to cause the one or more processors to execute the method of any of aspects 1-14.

16. A system comprising a memory storing instructions, and a processor configured to execute the instructions to perform the method of any of aspects 1-14.

17. A method for recommending, using a computing device, adjustments to treatment for a patient with diabetes based on a planned exercise session, the method comprising: receiving, by the computing device, input data indicative of (i) a future exercise start time at which the patient intends to begin exercising, (ii) a type of exercise that the patient intends to engage in, and (iii) an initial glucose value of the patient; presenting, via a display of the computing device, an initial recommendation to the user comprising at least one of an adjustment to a planned insulin bolus dose and an adjustment to a planned insulin basal rate, wherein the initial recommendation is based on at least one of the received type of exercise and the received initial glucose value; when a current time is within a first time period of the exercise start time, prompting, by the computing device, a user via the display to provide input indicative of a first scheduled glucose value of the patient; receiving, by the computing device, input data indicative of the first scheduled glucose value of the patient; determining, by the computing device, a second recommendation for the patient based on the received first scheduled glucose value; and presenting, via the display, the second recommendation.

18. The method of aspect 17, wherein determining the second recommendation comprises determining, based on the received first scheduled glucose value, at least one of a recommended amount of carbohydrates for the patient to consume, an adjustment to a planned insulin bolus dose, an adjustment to a planned insulin basal rate, and a new insulin bolus dose for an unplanned bolus administration.

19. The method of any of aspects 17-18, further comprising monitoring an on-board clock of the computing device to determine the current time.

20. The method of any of aspects 17-19, further comprising: when the current time is within a second time period of the exercise start time, wherein the second time period is shorter than the first time period, prompting a user via the display to provide input indicative of a second scheduled glucose value of the patient; receiving, at the computing device, input indicative of the second scheduled glucose value of the patient; determining, upon receipt of said second scheduled glucose value, a third recommendation for the patient based on the received second scheduled glucose level, the third recommendation comprising at least one of:

a recommended amount of carbohydrates for the patient to consume, an adjustment to a planned insulin bolus dose, an adjustment to a planned insulin basal rate, and a new insulin bolus dose for an unplanned bolus administration; and presenting, via the display, the third recommendation to the patient.

21. The method of any of aspects 17-20, further comprising:
receiving, at the computing device, input indicative of an exercise end time at which the patient intends to stop exercising; when the current time is equal to or greater than a third time period after the exercise end time, prompting the user via the display to provide input indicative of a third scheduled glucose value of the patient; receiving, at the computing device, input indicative of the third scheduled glucose value of the patient; and presenting upon receipt of said third scheduled glucose value, via the display, at least one of a recommendation to the patient to consume an amount of carbohydrates that is based on the third scheduled glucose value, a recommended adjustment to a planned insulin bolus dose, and a recommended adjustment to a planned insulin basal rate.

22. The method of aspect 21, wherein the first time period is one hour, the second time period is 15 minutes, and the third time period is 15 minutes.

23. The method of any of aspects 17-22, further comprising presenting, via the display, a visual timeline that includes a visual indicator indicating a time at which the user will be prompted to provide input indicative of the first scheduled glucose value, and a separate visual indicator indicating the future exercise start time.

24. The method of any of aspects 21-23, further comprising presenting, via the display, a visual timeline that includes: a visual indicator indicating a time at which the user will be prompted to provide input indicative of the first scheduled glucose value; a visual indicator indicating a time at which the user will be prompted to provide input indicative of the second scheduled glucose value; a visual indicator indicating the exercise start time; and a visual indicator indicating a time at which the user will be prompted to provide input indicative of the third scheduled glucose value.

25. The method of any of aspects 17-24, further comprising providing a push notification to the user after an exercise session that provides recommendations to the user for avoiding hypoglycemia when sleeping after the exercise session.

26. The method of aspect 25, wherein the push notification comprises at least one of a recommendation to increase the sensitivity of a hypoglycemia alarm on a glucose sensor while sleeping, a recommendation to consume at least one of proteins and fats, and a recommendation to take less insulin after the exercise session.

27. The method of any of aspects 17-26, further comprising presenting upon receipt of said first scheduled glucose value, via the display, a recommendation based on the received first scheduled glucose value that the patient limit exercise to aerobic exercises.

28. The method of any of aspects 21-27, further comprising presenting upon receipt of said third scheduled glucose value, via the display, a recommendation based on the received third scheduled glucose value that the patient conduct an aerobic cool-down.

29. A non-transitory computer-readable media comprising instructions that, when executed by one or more processors on a computing device, are operable to cause the one or more processors to execute the method of any of aspects 17-28.

30. A system comprising a memory storing instructions, and a processor configured to execute the instructions to perform the method of any of aspects 17-28.

31. A method for customizing a computerized exercise planning tool for developing, using a computing device, an exercise plan for a patient with diabetes, the method comprising: storing, by the computing device, a set of default rules associated with an exercise planning tool for developing an exercise plan for a patient with diabetes; receiving, by the computing device, input data indicative of a user preference for the exercise planning tool; modifying, by the computing device, an aspect of the exercise planning tool, comprising modifying the set of default rules to customize the exercise planning tool for the patient based on the input data; and generating, by the computing device, an exercise plan for the patient based on the modified aspect of the exercise planning tool, wherein the exercise plan is different than a second exercise plan that would have been generated using the unmodified set of default rules.

32. The method of aspect 31, wherein generating the exercise plan for the patient comprises: receiving second input data indicative of one or more of (i) a future exercise start time at which the patient intends to begin exercising, (ii) a type of exercise that the patient intends to engage in, and (iii) an initial glucose value of the patient, wherein the input data indicative of a user preference does not include any of (i), (ii) or (iii); and generating the exercise plan based on the received second input data and the modified aspect of the exercise planning tool.

33. The method of any of aspects 31-32, wherein receiving the input data comprises receiving data indicative of a user goal for the exercise plan.

34. The method of aspect 33, wherein the user goal comprises one or more of a goal to lose weight, a goal to maintain weight, a goal to build muscle, a goal to maintain muscle, a goal to train for a certain event, a goal to perform an exercise, a goal to improve flexibility, a goal to maintain flexibility, or some combination thereof 35. The method of any of aspects 31-34, wherein modifying comprises modifying the set of default rules to provide a customized recommendation during preparation for an exercise, wherein the customized recommendation is different than a default recommendation.

36. The method of any of aspects 31-35, wherein modifying comprises modifying the set of default rules to provide a customized recommendation during performance of an exercise, wherein the customized recommendation is different than a default recommendation.

37. The method of aspect 36, wherein providing the customized recommendation comprises: receiving second input data indicative of a glucose value of the patient while performing the exercise; determining the customized recommendation for the patient based on the second input data and the modified aspect of the exercise planning tool; and presenting, via a display of the computing device, the customized recommendation.

38. The method of aspect 37, wherein: determining the customized recommendation comprises determining, based on the second input data, the patient is at risk of hypoglycemia; the customized recommendation comprises a modification to the exercise; and the default recommendation comprises a recommendation to ingest carbohydrates.

39. The method of aspect 37, wherein: the default recommendation comprises a default bolus dose, a default basal rate, or some combination thereof; and the customized recommendation comprises a customized bolus dose that is different than the default bolus dose, a customized basal rate that is different than the default basal rate, or some combination thereof.

40. The method of any of aspects 31-39, wherein: generating the exercise plan for the patient based on the modified aspect of the exercise planning tool comprises sorting an original order of a set of recommended exercises to provide a set of preferred exercises at a beginning of the set of sorted recommendations so that the preferred exercises are presented to the patient before other exercises in the set of recommended exercises; and the second exercise plan that would have been generated using the unmodified set of default rules comprises providing the set of recommended exercises according to the original order of the set of recommended exercises.

41. A non-transitory computer-readable media comprising instructions that, when executed by one or more processors on a computing device, are operable to cause the one or more processors to execute the method of any of aspects 31-40.

42. A system comprising a memory storing instructions, and a processor configured to execute the instructions to perform the method of any of aspects 31-40.

43. A method for customizing a computerized exercise planning tool for developing, using a computing device, an exercise plan for a patient with diabetes, the method comprising: storing, by the computing device, a set of default rules associated with an exercise planning tool for developing an exercise plan for a patient with diabetes; planning, by the computing device, a set of exercise plans for the patient using the exercise planning tool, wherein each exercise plan is associated with an exercise; monitoring, by the computing device, data indicative of (i) a treatment aspect of the patient, (ii) a physiological aspect of the patient, or both, for each exercise plan in the set of exercise plans; modifying, by the computing device, the set of default rules to customize the exercise planning tool for the patient based on the monitored data; and generating, by the computing device, a new exercise plan for the patient based on the modified set of default rules, wherein the new exercise plan is different than an exercise plan that would have been generated using the unmodified set of default rules.

44. The method of aspect 43, wherein monitoring data indicative of the treatment aspect of the patient comprises monitoring data indicative of a set of insulin doses.

45. The method of any of aspects 43-44, wherein monitoring data indicative of the physiological aspect of the patient comprises monitoring a set of heartrate measurements, a set of glucose measurements, a set of activity measurements, a set of food ingestions, or some combination thereof.

46. The method of any of aspects 43-45, wherein the new exercise plan comprises at least one of: a bolus dose that is different than a bolus dose of the exercise plan that would have been generated using the unmodified set of default rules; and a basal rate that is different than a basal rate of the exercise plan that would have been generated using the unmodified set of default rules.

47. The method of any of aspects 43-46, wherein generating the new exercise plan comprises generating a recommended amount of carbohydrates for the patient to ingest that is different than an amount of carbohydrates recommended by the exercise plan that would have been generated using the unmodified set of default rules.

48. The method of any of aspects 43-47, wherein generating the new exercise plan comprises: predicting the patient's glucose response to a current exercise that the patient is currently engaged in based on the patient's heart rate during the current exercise; and recommending at least one of administration of a bolus dose of insulin, ingestion of an amount of carbohydrates, and a modified exercise different from the current exercise based on the predicted glucose response.

49. The method of any of aspects 43-48, wherein generating the new exercise plan comprises: storing an original set of classifications of exercises; generating a new set of classifications of the exercises, wherein the new set of classifications comprises more classifications than the original set of classifications; and generating the new exercise plan based on the new set of classifications.

50. The method of any of aspects 43-49, wherein generating the new exercise plan comprises sorting an original order of a set of recommended exercises to provide a set of preferred exercises at a beginning of the set of sorted recommendations so that the preferred exercises are presented to the patient before other exercises in the set of recommended exercises.

51. The method of any of aspects 43-50, wherein generating the new exercise plan comprises selecting a recommended exercise from a group of available exercises based on the monitored data.

52. A non-transitory computer-readable media comprising instructions that, when executed by one or more processors on a computing device, are operable to cause the one or more processors to execute the method of any of aspects 43-51.

53. A system comprising a memory storing instructions, and a processor configured to execute the instructions to perform the method of any of aspects 43-51.

54. A method for providing a recommendation to a patient with diabetes during an exercise using a computing device, the method comprising: receiving, by the computing device, input data indicative of (i) an exercise being conducted by the patient and (ii) a present glucose value of the patient while conducting the exercise; determining, by the computing device, one or more recommendations based on the present glucose value; and displaying, via a display of the computing device, the one or more recommendations.

55. The method of aspect 54, wherein determining the one or more recommendations comprises: determining, based on the input data, the exercise is an aerobic exercise; determining, based on the present glucose value, the patient's glucose levels are less than a minimum threshold value; and generating a recommendation for the patient to perform one or more anaerobic exercises.

56. The method of aspect 54, wherein determining the one or more recommendations comprises: determining, based on the input data, the exercise is an anaerobic exercise; determining, based on the present glucose value, the patient's glucose levels are greater than a maximum threshold value; and generating a recommendation for the patient to perform one or more aerobic exercises.

57. The method of aspect 54, wherein determining the one or more recommendations comprises: determining, based on the input data, the exercise is a mixed aerobic and anaerobic exercise; determining, based on the present glucose value, a change in the patient's glucose level relative to a previous glucose value; generating a recommendation for the patient based on the determined change in the patient's glucose level.

58. A non-transitory computer-readable media comprising instructions that, when executed by one or more processors on a computing device, are operable to cause the one or more processors to execute the method of any of aspects 54-57.

59. A system comprising a memory storing instructions, and a processor configured to execute the instructions to perform the method of any of aspects 54-57.

What is claimed is:

1. A method for recommending one or more types of exercise to a patient with diabetes using a computing device, the method comprising:
   receiving, by the computing device, input data indicative of (i) a future exercise start time at which the patient intends to begin exercising and (ii) a present glucose value of the patient;
   determining, by the computing device, an amount of time between a present time and the future exercise start time;
   determining, by the computing device, one or more recommended exercise types based on the present glucose value of the patient and the amount of time, wherein determining the one or more recommended exercise types comprises,
   when the amount of time is less than or equal to a minimum duration threshold:
      determining whether the present glucose value is less than a first glucose threshold,
      selecting a first plurality of exercise types from a first category of exercises as the determined one or more recommended exercise types if the present glucose value is less than the first glucose threshold, wherein the first category of exercises consists of anaerobic exercises, and
      selecting a second plurality of exercise types from a second category of exercises as the determined one or more recommended exercise types if the present glucose value is greater than or equal to the first glucose threshold, wherein the second category of exercises consists of aerobic exercises, and wherein the first plurality of exercise types is different from the second plurality of exercise types; and
   when the amount of time is greater than the minimum duration threshold:
      selecting both the first plurality of exercise types from the first category of exercises and the second plurality of exercise types from the second category of exercises as the determined one or more recommended exercise types; and
   displaying, via a display of the computing device, the one or more recommended exercise types, wherein a likelihood of the patient experiencing hypoglycemia or hyperglycemia during exercise is reduced when the patient engages in one of the recommended exercise types.

2. The method of claim 1, wherein determining the one or more recommended exercise types comprises, when the amount of time is less than the minimum duration threshold, including a third plurality of exercise types from a third category of exercises into the determined one or more recommended exercise types if the present glucose value is between a second glucose threshold and a third glucose threshold.

3. The method of claim 2, wherein determining the one or more recommended exercise types comprises selecting the first plurality of exercise types from the first category of exercises, the second plurality of exercise types from the second category of exercises, and the third plurality of exercise types from the third category of exercises as the determined one or more recommended exercise types when the amount of time is greater than or equal to the minimum duration threshold.

4. The method of claim 1, wherein the minimum duration threshold is one hour.

5. The method of claim 2, wherein the third category of exercises comprises mixed aerobic and anaerobic exercises.

6. The method of claim 1, wherein the first glucose threshold is between 130 mg/dL and 160 mg/dL.

7. The method of claim 1, wherein the first glucose threshold is between 140 mg/dL and 150 mg/dL.

8. The method of claim 2, wherein the second glucose threshold is between 80 mg/dL and 120 mg/dL, and the third glucose threshold is between 140 mg/dL and 180 mg/dL.

9. The method of claim 2, wherein the second glucose threshold is between 95 mg/dL and 105 mg/dL, and the third glucose threshold is between 155 mg/dL and 165 mg/dL.

10. The method of claim 1, wherein the computing device receives the present glucose value of the patient from at least one of a connected glucose meter and manual user input.

11. The method of claim 1, further comprising receiving second input data indicative of an Insulin on Board (IOB) amount for the patient, and wherein the one or more recommended exercise types is determined based at least in part on the second input data.

12. A non-transitory computer-readable media comprising instructions that, when executed by one or more processors on a computing device, are operable to cause the one or more processors to:
   receive input data indicative of (i) a future exercise start time at which a patient intends to begin exercising and (ii) a present glucose value of the patient;
   determine an amount of time between a present time and the future exercise start time;
   determine one or more recommended exercise types based on the present glucose value of the patient and the amount of time, wherein determining the one or more recommended exercise types comprises,
   when the amount of time is less than or equal to a minimum duration threshold:
      determining whether the present glucose value is less than a first glucose threshold,
      selecting a first plurality of exercise types from a first category of exercises as the determined one or more recommended exercise types if the present glucose value is less than the first glucose threshold, wherein the first category of exercises consists of anaerobic exercises, and
      selecting a second plurality of exercise types from a second category of exercises as the determined one or more recommended exercise types if the present glucose value is greater than or equal to the first glucose threshold, wherein the second category of exercises consists of aerobic exercises, and wherein the first plurality of exercise types is different from the second plurality of exercise types; and
   when the amount of time is greater than the minimum duration threshold:
      selecting both the first plurality of exercise types from the first category of exercises and the second plurality of exercise types from the second category of exercises as the determined one or more recommended exercise types; and
   display, via a display of the computing device, the one or more recommended exercise types, wherein a likelihood of the patient experiencing hypoglycemia or hyperglycemia during exercise is reduced when the patient engages in one of the recommended exercise types.

13. The non-transitory computer-readable media of claim 12, wherein determining the one or more recommended exercise types comprises, when the amount of time is less than the minimum duration threshold, including a third plurality of exercise types from a third category of exercises into the determined one or more recommended exercise types if the present glucose value is between a second glucose threshold and a third glucose threshold.

14. The non-transitory computer-readable media of claim 13, wherein determining the one or more recommended exercise types comprises selecting the first plurality of exercise types from the first category of exercises, the second plurality of exercise types from the second category of exercises, and the third plurality of exercise types from the third category of exercises as the determined one or more recommended exercise types when the amount of time is greater than or equal to the minimum duration threshold.

15. The non-transitory computer-readable media of claim 13 wherein the third category of exercises comprises mixed aerobic and anaerobic exercises.

16. The non-transitory computer-readable media of claim 12, wherein the instructions are further operable to cause the one or more processors to receive second input data indicative of an Insulin on Board (IOB) amount for the patient, and wherein the one or more recommended exercise types is determined based at least in part on the second input data.

17. A system comprising a memory storing instructions, and a processor on a computing device configured to execute the instructions to:
 receive input data indicative of (i) a future exercise start time at which a patient intends to begin exercising and (ii) a present glucose value of the patient;
 determine an amount of time between a present time and the future exercise start time;
 determine one or more recommended exercise types based on the present glucose value of the patient and the amount of time, wherein determining the one or more recommended exercise types comprises,
 when the amount of time is less than or equal to a minimum duration threshold:
  determining whether the present glucose value is less than a first glucose threshold,
  selecting a first plurality of exercise types from a first category of exercises as the determined one or more recommended exercise types if the present glucose value is less than the first glucose threshold, wherein the first category of exercises consists of anaerobic exercises, and
  selecting a second plurality of exercise types from a second category of exercises as the determined one or more recommended exercise types if the present glucose value is greater than or equal to the first glucose threshold, wherein the second category of exercises consists of aerobic exercises, and wherein the first plurality of exercise types is different from the second plurality of exercise types; and
 when the amount of time is greater than the minimum duration threshold:
  selecting both the first plurality of exercise types from the first category of exercises and the second plurality of exercise types from the second category of exercises as the determined one or more recommended exercise types; and
 display, via a display of the computing device, the one or more recommended exercise types, wherein a likelihood of the patient experiencing hypoglycemia or hyperglycemia during exercise is reduced when the patient engages in one of the recommended exercise types.

18. The system of claim 17, wherein determining the one or more recommended exercise types comprises, when the amount of time is less than the minimum duration threshold, including a third plurality of exercise types from a third category of exercises into the determined one or more recommended exercise types if the present glucose value is between a second glucose threshold and a third glucose threshold.

19. The system of claim 18, wherein determining the one or more recommended exercise types comprises selecting the first plurality of exercise types from the first category of exercises, the second plurality of exercise types from the second category of exercises, and the third plurality of exercise types from the third category of exercises as the determined one or more recommended exercise types when the amount of time is greater than or equal to the minimum duration threshold.

20. The system of claim 18, wherein the third category of exercises comprises mixed aerobic and anaerobic exercises.

21. The system of claim 17, wherein the processor is further configured to execute the instructions to receive second input data indicative of an Insulin on Board (IOB) amount for the patient, and wherein the one or more recommended exercise types is determined based at least in part on the second input data.

* * * * *

UNITED STATES PATENT AND TRADEMARK OFFICE
CERTIFICATE OF CORRECTION

| | | |
|---|---|---|
| PATENT NO. | : 12,327,639 B2 | Page 1 of 1 |
| APPLICATION NO. | : 17/598539 | |
| DATED | : June 10, 2025 | |
| INVENTOR(S) | : Stephanie Smith Edwards et al. | |

It is certified that error appears in the above-identified patent and that said Letters Patent is hereby corrected as shown below:

On the Title Page

Item (57) In the Abstract, on Page 2, Column 1, Line 2:
Delete "patients" and insert -- patient's --.

Signed and Sealed this
Twenty-eighth Day of October, 2025

John A. Squires
*Director of the United States Patent and Trademark Office*